(12) United States Patent
Shiraishi

(10) Patent No.: US 8,945,802 B2
(45) Date of Patent: Feb. 3, 2015

(54) FLARE-MEASURING MASK, FLARE-MEASURING METHOD, AND EXPOSURE METHOD

(75) Inventor: Masayuki Shiraishi, Kawasaki (JP)

(73) Assignee: Nikon Corporation, Tokyo (JP)

( * ) Notice: Subject to any disclaimer, the term of this patent is extended or adjusted under 35 U.S.C. 154(b) by 324 days.

(21) Appl. No.: 12/654,438

(22) Filed: Dec. 18, 2009

(65) Prior Publication Data

US 2010/0227261 A1    Sep. 9, 2010

Related U.S. Application Data

(60) Provisional application No. 61/202,478, filed on Mar. 3, 2009.

(51) Int. Cl.
*G03F 7/20* (2006.01)
*G06F 17/50* (2006.01)
*G01N 21/59* (2006.01)
*G03F 1/00* (2012.01)
*G03F 1/44* (2012.01)

(52) U.S. Cl.
CPC  *G03F 1/14* (2013.01); *G03F 1/144* (2013.01); *G03F 1/44* (2013.01); *G03F 7/70941* (2013.01)
USPC .............................. 430/30; 716/50; 356/124

(58) Field of Classification Search
CPC ...................................................... G01N 21/49
USPC ................. 356/302, 124, 432, 239.2; 716/50; 430/30
See application file for complete search history.

(56) References Cited

U.S. PATENT DOCUMENTS

| | | | |
|---|---|---|---|
| 6,986,973 B2 | 1/2006 | Yao et al. | |
| 2005/0270523 A1* | 12/2005 | Wu et al. | 356/237.5 |
| 2006/0080046 A1* | 4/2006 | Ziger et al. | 702/32 |
| 2006/0285124 A1* | 12/2006 | Hill | 356/511 |

(Continued)

FOREIGN PATENT DOCUMENTS

| | | |
|---|---|---|
| JP | A-06-302492 | 10/1994 |
| JP | A-2006-80245 | 3/2006 |
| JP | A-2007-234716 | 9/2007 |

(Continued)

OTHER PUBLICATIONS

Lee et al., Anisotropic EUV flare measured in the Engineering Test Stand (ETS), Proceedings of SPIE vol. 5374, SPIE, Bellingham, WA, 2004.

(Continued)

*Primary Examiner* — Mark F Huff
*Assistant Examiner* — John S Ruggles
(74) *Attorney, Agent, or Firm* — Oliff PLC

(57) ABSTRACT

A method for measuring flare information of a projection optical system includes arranging, on an object plane of the projection optical system, a sectoral pattern surrounded by a first side, a second side which is inclined at a predetermined angle with respect to the first side, and an inner diameter portion and an outer diameter portion which connect both ends of the first side and both ends of the second side; projecting an image of the sectoral pattern via the projection optical system; and determining the flare information based on a light amount of the image of the sectoral pattern and a light amount provided at a position away from the image. With the flare measuring method, it is possible to correctly measure the flare information in an arbitrary angle range of the sectoral pattern.

17 Claims, 9 Drawing Sheets

(56) References Cited

U.S. PATENT DOCUMENTS

2008/0068595 A1 3/2008 Hagiwara
2008/0206654 A1* 8/2008 Abe .............................. 430/311

FOREIGN PATENT DOCUMENTS

| JP | A-2008-288338 | 11/2008 |
| WO | A1-WO2005/008754 | 1/2005 |
| WO | WO 2005/008754 A1 | 1/2005 |

OTHER PUBLICATIONS

"Lithographic flare measurements of Intel's microexposure tool optics;" *J. Vac. Sci. Technol.*; Jan./Feb. 2006; vol. B24, No. 1; American Vacuum Society, Chandhok et al., pp. 274-278.

Lee et al.; "Lithographic flare measurements of EUV full-field projection optics;" *Emerging Lithographic Technologies VII, Proceedings of SPIE*; 2003; pp. 103-111; vol. 5037; SPIE.

International Search Report dated Jun. 30, 2010 in corresponding International Application No. PCT/JP2010/052802.

Written Opinion of the International Searching Authority dated Jun. 30, 2010 in corresponding International Application No. PCT/JP2010/052802.

Oct. 16, 2013 Office Action issued in Japanese Patent Application No. 2010-043197 (with translation).

Jul. 3, 2014 Office Action issued in Taiwanese Patent Application No. 098145704 (with translation).

Mar. 4, 2014 Office Action issued in Japanese Patent Application No. 2010-043197 (with translation).

\* cited by examiner

Fig. 4A
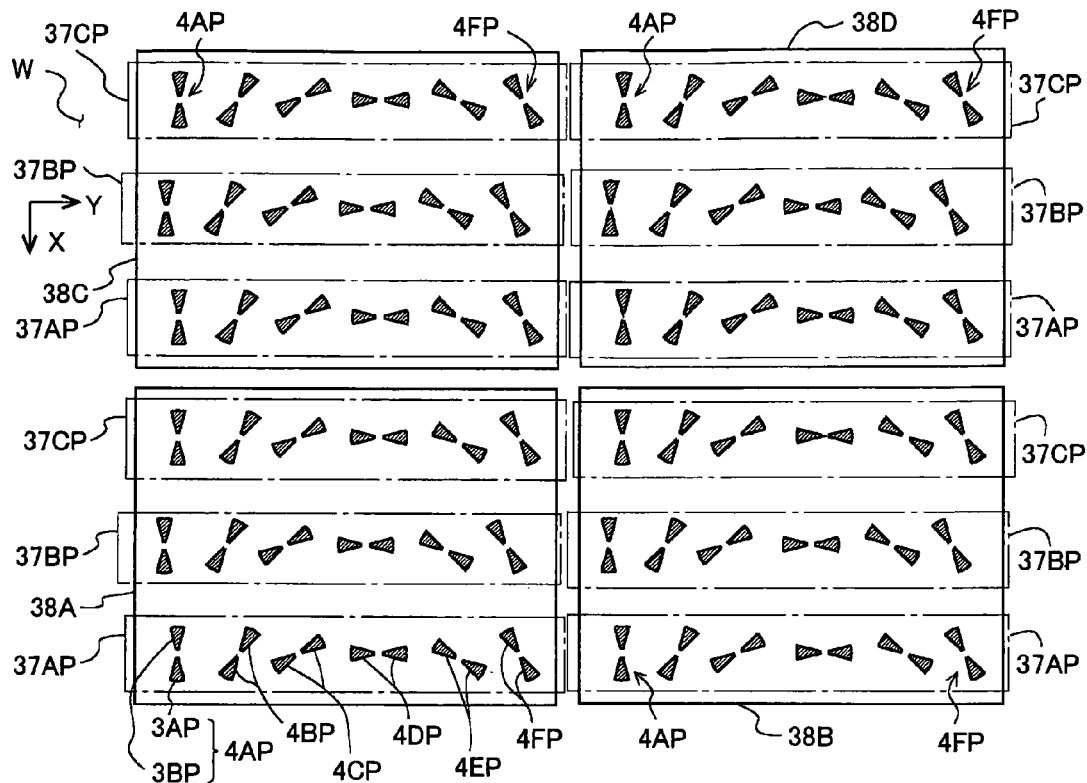
Fig. 4B         Fig. 4C         Fig. 4D
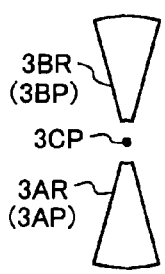 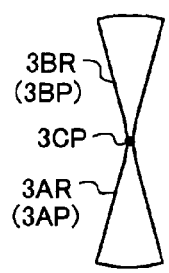 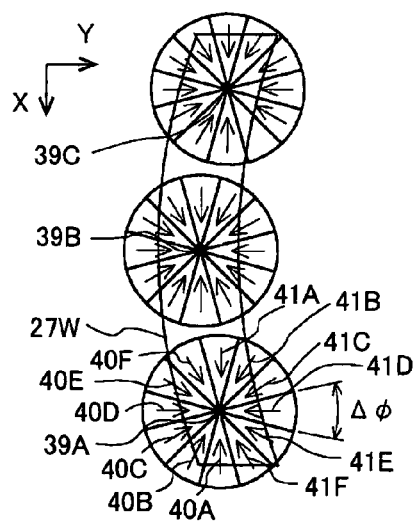

FLARE-MEASURING MASK, FLARE-MEASURING METHOD, AND EXPOSURE METHOD

CROSS-REFERENCES TO RELATED APPLICATIONS

This application claims the benefit of priority of U.S. Provisional Application No. 61/202,475 filed on Mar. 3, 2009, the entire disclosures of which are incorporated herein by reference.

BACKGROUND OF THE INVENTION

1. Field of the Invention

The present invention relates to a flare-measuring method for measuring flare information of a projection optical system, a flare-measuring mask usable to carry out the flare-measuring method, a mask pattern-correcting method using the flare-measuring method, and an exposure method using the flare-measuring method.

2. Description of the Related Art

In an exposure apparatus which is used in the photolithography step of producing various devices (electronic devices) including semiconductor devices, etc., if a scattered light, which is generated due to the surface roughness of an optical member constructing a projection optical system, forms any flare as a blur of an image around the image to be imaged by the genuine light flux, then the contrast of the image is lowered, and the imaging characteristic is affected thereby. Accordingly, the flare of the projection optical system is measured beforehand; and for example, a shape of a pattern of a reticle (mask) is corrected depending on a result of the measurement to form a target pattern on a wafer (or a glass plate or the like) as the exposure objective. In the case of an exposure apparatus (EUV exposure apparatus) which uses, as the exposure light (exposure light beam), an extreme ultraviolet light or extreme ultraviolet light beam (hereinafter referred to as "EUV light") having a wavelength of not more than about 100 nm, almost all of optical members including the reticle are reflecting members, wherein the flare tends to appear with ease, while the required resolution is heightened. Therefore, it is necessary to measure the flare highly accurately.

The Kirk method is known as a conventional flare-measuring method, wherein an image of an evaluating pattern, which includes, for example, an annular or zonal transmitting portion (or reflecting portion), is subjected to the exposure via a projection optical system, and the flare is evaluated based on the ratio of an exposure amount provided when an image of the transmitting portion is subjected to the exposure with respect to an exposure amount provided when a center of an image of a light shielding portion disposed inside the transmitting portion is subjected to the exposure (see, for example, Japanese Patent Application Laid-open No. 2007-234716). Recently, in order to further evaluate the flare in each of distinct directions, a flare-measuring method has been also suggested, wherein pairs of bar-shaped patterns are arranged while being directed or oriented in four different directions, and the flare amount is determined for an image of a central gap portion of each of the pairs of bar-shaped patterns directed in one of the different directions (see, for example, Japanese Patent Application Laid-open No. 2008-288338).

According to the conventional flare-measuring method in which the pairs of bar-shaped patterns are arranged while being directed or oriented in the different directions, it is possible to compare the differences (anisotropies) in the distinct directions of the flares. However, even if a large number of the pairs of bar-shaped patterns are arranged while being directed in the different directions, a problem arises such that an area, at which no bar-shaped pattern is arranged, is increased at positions away or separated farther from the measuring point on the image plane, and it is difficult to evaluate the contribution of the flare in relation to all directions.

SUMMARY OF THE INVENTION

Taking the foregoing circumstances into consideration, an object of the present invention is to provide a flare-measuring technique which makes it possible to correctly measure the flare information in an arbitrary angle range, a mask pattern-correcting technique using the flare-measuring technique, and an exposure technique using the flare-measuring technique.

According to a first aspect of the present invention, there is provided a flare-measuring mask comprising at least one aperture pattern having a first straight line portion, a second straight line portion which is inclined at a predetermined angle with respect to the first straight line portion, and a first connecting portion which connects one end of the first straight line portion and one end of the second straight line portion.

According to a second aspect of the present invention, there is provided a flare-measuring mask having a predetermined pattern and used to measure a flare of an optical system from an image of the predetermined pattern which is projected via the optical system by being irradiated with a radiation, wherein the predetermined pattern includes: a first area which is extended in a radial direction from a predetermined position away from a rotational center in the radial direction and which is spread about the rotational center at a predetermined opening angle; a second area which has a shape same as that of the first area and which is arranged symmetrically to the first area with respect to the rotational center; and a block area including the rotational center, located between the first and second areas and having an opposite characteristic regarding transmissivity or reflectivity with respect to the radiation to that of the first and second areas.

According to a third aspect of the present invention, there is provided a flare-measuring method for measuring flare information of a projection optical system, the flare-measuring method comprising: arranging, on an object plane of the projection optical system, an aperture pattern having a first straight line portion, a second straight line portion which is inclined at a predetermined angle with respect to the first straight line portion, and a first connecting portion which connects one end of the first straight line portion and one end of the second straight line portion; irradiating (radiating) an exposure light onto the aperture pattern and projecting an image of the aperture pattern via the projection optical system; and determining the flare information based on a ratio of a light amount of the exposure light irradiated (radiated) onto the aperture pattern with respect to a light amount of the image of the aperture pattern provided via the projection optical system.

According to a fourth aspect of the present invention, there is provided a flare-measuring method for measuring flare information of an optical system, the flare-measuring method comprising:

arranging, on an object plane of the optical system, a mask including a predetermined pattern having: a first area which is extended in a radial direction from a predetermined position away from a rotational center in the radial direction and which is spread about the rotational center at a predetermined opening angle; a second area which has a shape same as that of the first area and which is arranged symmetrically to the first area with respect to the rotational center; and a block area including the rotational center, located between the first and second areas and having an opposite characteristic regarding transmissivity or reflectivity with respect to a radiation to that of the first and second areas;

irradiating the radiation onto the mask to project an image of the pattern via the optical system; and determining the flare information by observing projected images of the first and second area or a projected image of the block area.

According to another aspect of the present invention, there is provided a mask pattern-correcting method for correcting a pattern, of a mask, which is to be projected by a projection optical system, the mask pattern-correcting method comprising: measuring flare information of the projection optical system by the flare-measuring method of the present invention; and correcting the pattern based on a measurement result of the flare information.

According to still another aspect of the present invention, there is provided an exposure method for illuminating a pattern or a pattern of a patterning mask with an exposure light or a radiation and exposing an object with the exposure light via the pattern and a projection optical system or an optical system, the exposure method comprising: measuring flare information of the projection optical system by the flare-measuring method of the present invention; correcting the pattern as a transfer objective based on a measurement result of the flare information; and exposing the object with the exposure light via the projection optical system and the corrected pattern as the transfer objective.

According to the flare-measuring method of the present invention, by projecting the image of the aperture pattern, it is possible to correctly measure the flare information within a range of the opening angle (predetermined angle) of the aperture pattern and further to easily process the measurement result on the polar coordinate system, if necessary.

According to the flare-measuring mask of the present invention, the aperture pattern thereof can be used when the flare-measuring method of the present invention is carried out.

BRIEF DESCRIPTION OF THE DRAWINGS

FIG. 4A is a plan view of images of the pattern of the test reticle exposed on a plurality of shot areas, respectively, on a wafer; FIG. 4B shows a magnified plan view illustrating a part of a resist pattern formed on the wafer after the development; FIG. 4C is a magnified plan view illustrating a state that resist patterns corresponding to an image of a pair of the sectoral patterns are connected to each other; and FIG. 4D shows the flares in all of directions at a plurality of measuring points in an exposure area.

DESCRIPTION OF THE PREFERRED EMBODIMENTS

An exemplary embodiment of the present invention will be explained with reference to FIGS. 1 to 6 by way of example.

Figure 1:
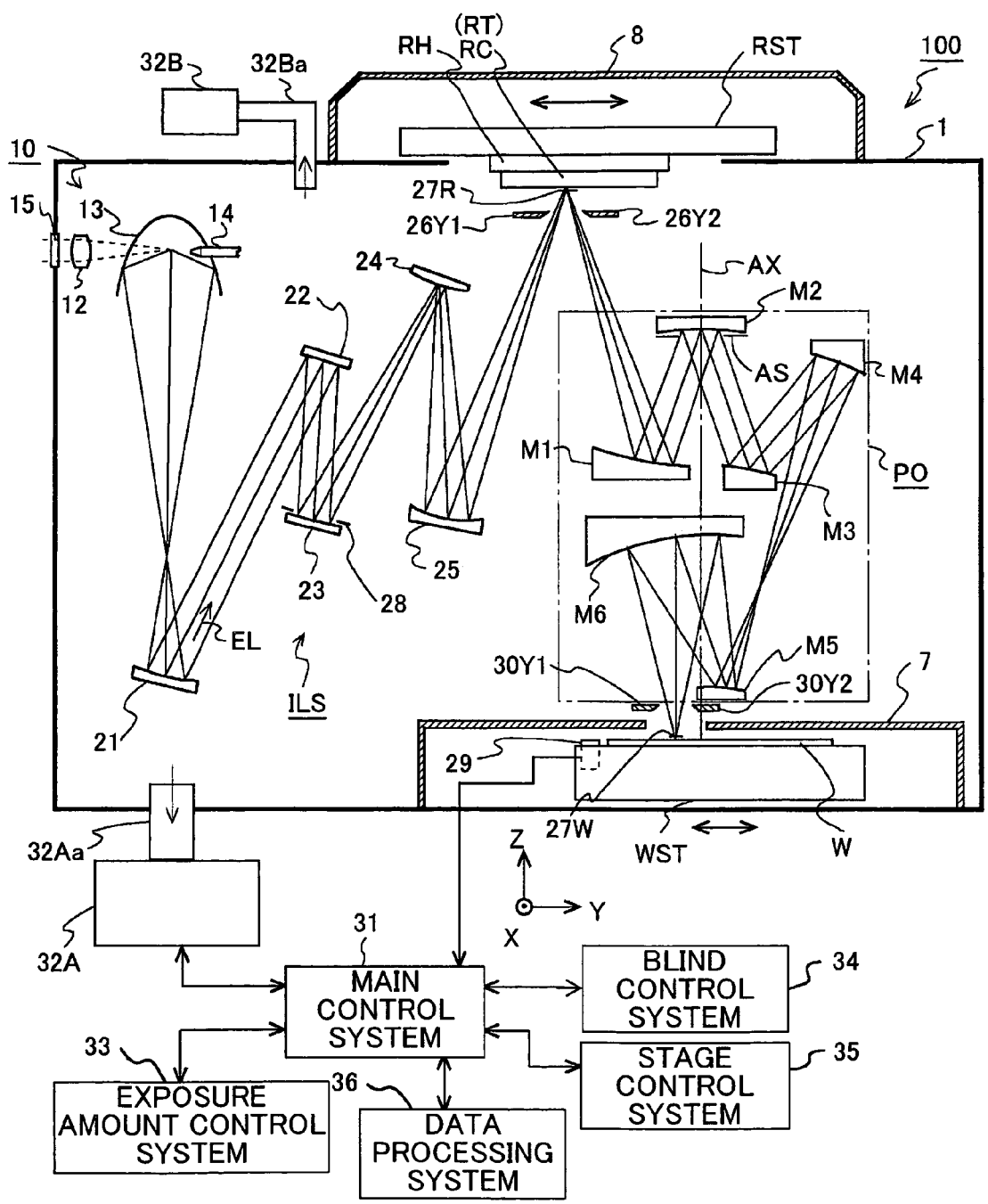
FIG. 1 is a sectional view of a schematic construction of an exemplary exposure apparatus according to an embodiment of the present invention.

FIG. 1 is a sectional view schematically illustrating the overall construction of an exposure apparatus 100 of this embodiment. The exposure apparatus 100 is an EUV exposure apparatus which uses, as the exposure light (exposure light beam or illumination light (illumination light beam) for the exposure) EL, the EUV light (Extreme Ultraviolet Light) having a wavelength that is not more than about 100 nm and within a range of about 3 to 50 nm, for example, having a wavelength of 11 nm or 13 nm. With reference to FIG. 1, the exposure apparatus 100 includes a laser plasma light source 10 which pulse-generates the exposure light EL, an illumination optical system ILS which illuminates a pattern surface (lower surface in this embodiment) of a reticle RC (mask) in an illumination area 27R with the exposure light EL, a reticle stage RST which moves the reticle RC, and a projection optical system PO which projects an image of a pattern included in the illumination area 27R of the reticle RC onto a wafer W (photosensitive substrate) coated with a resist (photosensitive material). The exposure apparatus 100 further includes a wafer stage WST which moves the wafer W, a main control system 31 which includes a computer integrally controlling the operation of the entire apparatus; and the like.

In this embodiment, the EUV light is used as the exposure light (radiation) EL. Therefore, each of the illumination optical system ILS and the projection optical system (optical system) PO is constructed of a plurality of catoptric optical members such as mirrors or the like, except for a specific filter or the like (not shown), and the reticle RC is also of the catoptric or reflecting type. The catoptric optical member has a reflecting surface obtained, for example, such that a surface of a member, which is composed of silica glass (or highly heat resistant metal or the like), is processed highly accurately into a predetermined curved surface or flat surface, and then a multilayered film (reflective film for the EUV light), which is composed of molybdenum (Mo) and silicon (Si), is formed on the surface to provide the reflecting surface. The multilayered film may be another multilayered film obtained by combining a substance such as ruthenium (Ru), rhodium (Rh) or the like and a substance such as Si, beryllium (Be), carbon tetraboride ($B_4C$) or the like. The reticle RC is prepared as follows. That is, for example, a multilayered film is formed on a surface of a substrate made of silica glass to provide a reflecting surface (reflective film). After that, a transfer pattern is formed on the reflecting surface with an absorbing layer composed of a material absorbing the EUV light, including, for example, tantalum (Ta), nickel (Ni), chromium (Cr) and the like.

In order to avoid the absorption of the EUV light by a gas, the exposure apparatus 100 is accommodated in a box-shaped vacuum chamber 1 approximately as a whole. For example, large-sized vacuum pumps 32A, 32B are provided in order to perform the vacuum evacuation for the space in the vacuum chamber 1, for example, via gas discharge tubes 32Aa, 32Ba. Further, a plurality of subchambers (not shown) are also provided in order to further enhance the degree of vacuum on the optical path for the exposure light EL in the vacuum chamber 1. For example, the vacuum chamber 1 has an internal gas pressure of about $10^{-5}$ Pa, and a subchamber (not shown), which accommodates the projection optical system PO in the vacuum chamber 1, has an internal gas pressure of about $10^{-5}$ to $10^{-6}$ Pa.

Figure 2A:
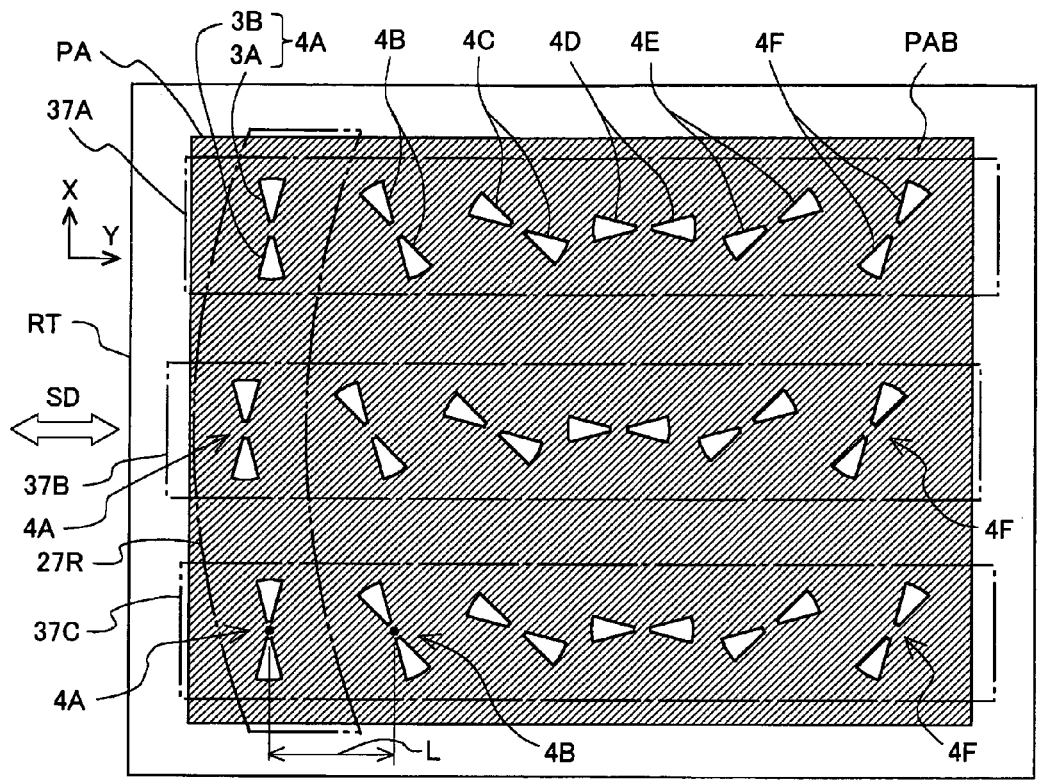
FIG. 2A is a bottom view of an exemplary arrangement of a plurality of evaluating patterns disposed on a test reticle.

The following description will be made assuming that the Z axis extends in the normal line direction of the surface (bottom surface of the vacuum chamber 1) on which the wafer stage WST is placed as shown in FIG. 1; the X axis extends perpendicularly to the sheet surface of FIG. 1 in a plane perpendicular to the Z axis (plane substantially parallel to the horizontal surface in this embodiment); and the Y axis extends in parallel to the sheet surface of FIG. 1. In this embodiment, the illumination area 27R is formed on the reticle RC when the exposure light EL is irradiated (radiated) onto the reticle RC. The illumination area 27R has a circular arc-shaped form which is long in the X direction (non-scanning direction) as shown in FIG. 2A. During the ordinary exposure, the reticle RC and the wafer W are synchronously scanned in the Y direction (scanning direction) with respect to the projection optical system PO.

At first, the laser plasma light source 10 is a light source of the gas jet cluster system including a high output laser light source (not shown); a light-collecting lens 12 which collects the laser beam supplied from the laser light source via a window member 15 of the vacuum chamber 1; a nozzle 14 which jets a target gas of for example, xenon; and a light-collecting mirror 13 which has a spheroidal plane-shaped reflecting surface. The exposure light EL, which is pulse-emitted at a frequency of, for example, several kHz from the laser plasma light source 10, is focused or collected on the second focal point of the light-collecting mirror 13. The output of the laser plasma light source 10 (radiation energy or irradiation energy of the exposure light EL per unit time) is controlled by an exposure amount control system 33 which is under the control of the main control system 31.

The exposure light EL, which is focused or collected on the second focal point, is substantially converted into a parallel light flux via a concave mirror (collimator optical system) 21, and comes into a first fly's eye optical system 22 constructed of a plurality of mirrors. The exposure light EL, reflected by the first fly's eye optical system 22, comes into a second fly's eye optical system 23 constructed of a plurality of mirrors. An optical integrator is constructed by the pair of fly's eye optical systems 22, 23. The illumination light coming from the laser plasma light source 10 effects the Koehler illumination for the first fly's eye optical system 22. The shapes, the arrangement, and other features of the respective mirror elements of the fly's eye optical systems 22, 23 are disclosed, for example, in U.S. Pat. No. 6,452,661. The contents of U.S. Pat. No. 6,452, 661 are incorporated herein by reference.

With reference to FIG. 1, the reflecting surfaces of the respective mirror elements of the first fly's eye optical system 22 are substantially conjugate with the pattern surface of the reticle RC; and a substantial surface light source (set or combination of a large number of minute secondary light sources), which has a predetermined shape, is formed in the vicinity of the reflecting surface of the second fly's eye optical system 23 (in the vicinity of the light-exit surface of the optical integrator). That is, a plane, on which the substantial surface light source is formed, is the pupil plane of the illumination optical system ILS. An aperture diaphragm 28 is arranged at the pupil plane or at a position in the vicinity of the pupil plane to switch the illumination condition, for example, into the ordinary illumination, the annular illumination, the dipole illumination, or the quadruple illumination.

The exposure light EL, passing through the aperture diaphragm 28, comes into a curved mirror 24. The exposure light EL reflected by the curved mirror 24 is reflected by a concave mirror 25. After that, the exposure light EL illuminates the circular arc-shaped illumination area 27R of the pattern surface of the reticle RC obliquely from a lower position at a uniform illuminance distribution in a superimposed or overlay manner. A condenser optical system is constructed by the curved mirror 24 and the concave mirror 25. The illumination optical system ILS is constructed to include the concave mirror 21, the fly's eye optical systems 22, 23, the aperture diaphragm 28, the curved mirror 24, and the concave mirror 25. In this case, the exposure light EL, which comes from the laser plasma light source 10, effects the Koehler illumination for the first fly's eye optical system 22 as well as the pattern surface of the reticle RC. The illumination optical system ILS is not limited to the construction shown in FIG. 1, and can be constructed in other various forms.

Further, a reticle blind (variable field diaphragm) is provided in order to define the circular arc-shaped illumination area 27R with respect to the pattern surface of the reticle RC. The reticle blind includes a first Y axis blind 26Y1 which shields an outer (−Y direction) edge portion of the exposure light EL, a second Y axis blind 26Y2 which shields an outer (+Y direction) edge portion of the exposure light EL reflected by the reticle RC; and first and second X axis blinds (not shown) defining the position and the width in the X direction of the illumination area 27R with respect to the pattern surface of the reticle RC. The opening/closing operation of the reticle blind is controlled by a blind control system 34 which is under the control of the main control system 31. The reticle blind of this embodiment forms a circular arc-shaped aperture (slit).

Further, the reticle RC is attracted and held on the bottom surface of the reticle stage RST via an electrostatic chuck RH. Based on the measured value obtained by a laser interferometer (not shown) and a control information of the main control system 31, the reticle stage RST is driven by a stage control system 35 at a predetermined stroke in the Y direction via a driving system (not shown), which is constructed of for example a magnetically floating type two-dimensional linear actuator, along a guide surface parallel to the XY plane of the outer surface of the vacuum chamber 1, and the reticle stage RST is also driven in a minute amount, for example, in the X direction and a direction of rotation about the Z axis (θZ direction). The reticle RC is placed (disposed) in the space surrounded by the vacuum chamber 1 through an opening of the upper surface of the vacuum chamber 1. A partition 8 is provided to cover the reticle stage RST on the side of the vacuum chamber 1. The interior of the partition 8 is maintained at a gas pressure between the atmospheric pressure and a gas pressure in the vacuum chamber 1 by an unillustrated vacuum pump.

The exposure light EL, which is reflected by the illumination area 27R of the reticle RC, is allowed to travel to the projection optical system PO forming a reduction image of the pattern of the object plane (first plane) on the image plane (second plane). The projection optical system PO is constructed, for example, such that six mirrors M1 to M6 are held by an unillustrated barrel; and the projection optical system PO is a catoptric system which is non-telecentric on the side of the object plane (pattern surface of the reticle RC) and which is substantially telecentric on the side of the image plane (surface of the wafer W). The projection magnification is a reduction magnification of ¼-fold, etc. The exposure light EL, which is reflected by the illumination area 27R of the reticle RC, forms the reduction image of a part of the pattern of the reticle RC in an exposure area 27W (area conjugate with the illumination area 27R) on the wafer W via the projection optical system PO.

In the projection optical system PO, the exposure light EL from the reticle RC is reflected by the first mirror M1 in the upward direction (+Z direction). Subsequently, the exposure light EL is reflected by the second mirror M2 in the downward direction. After that, the exposure light EL is reflected by the third mirror M3 in the upward direction, and the exposure light EL is reflected by the fourth mirror M4 in the downward direction. Subsequently, the exposure light EL, which is reflected by the fifth mirror M5 in the upward direction, is reflected by the sixth mirror M6 in the downward direction to form the image of the part of the pattern of the reticle RC on the wafer W. For example, the projection optical system PO is a coaxial optical system in which the optical axes of the mirrors, M1 to M6 are commonly overlapped with the optical axis AX. An aperture diaphragm AS is arranged on the pupil plane disposed in the vicinity of the reflecting surface of the mirror M2 or at a position in the vicinity of the pupil plane. A light shielding mechanism is provided between the mirror M6 and the wafer W, which includes a pair of light shielding plates 30Y1 and 30Y2 in the Y direction and a pair of light shielding plates in the X direction (not shown) in order to shield, for example, the flare generated by the scattering in the projection optical system PO. It is not necessarily indispensable that the projection optical system PO is the coaxial optical system. The projection optical system PO may be arbitrarily constructed.

Further, the wafer W is attracted and held on the wafer stage WST via an electrostatic chuck WH. The wafer stage WST is arranged on a guide surface arranged along the XY plane. Based on the measured value obtained by a laser interferometer (not shown) and a control information of the main control system 31, the wafer stage WST is driven by the stage control system 35 at predetermined strokes in the X direction and the Y direction via a driving mechanism (not shown) constructed of, for example, a magnetically floating type two-dimensional linear actuator, and the wafer stage WST is also driven in the θz direction, etc. if necessary.

An irradiation amount monitor 29, which is constructed of, for example, a photoelectric sensor such as a photodiode or the like having the sensitivity with respect to the EUV light, is arranged in the vicinity of the wafer W on the wafer stage WST. A detection signal of the irradiation amount monitor 29 is supplied to the main control system 31. For example, during the ordinary exposure, based on the measurement result obtained by the irradiation amount monitor 29, the main control system 31 controls the oscillation frequency and the pulse energy of the laser plasma light source 10 via the exposure amount control system 33, and the main control system 31 controls, for example, the scanning velocity of the reticle stage RST (and the wafer stage WST) via the stage control system 35 so that the totalized amount of exposure after the scanning exposure is included within an allowable range at each of the points on the wafer W. A data processing system 36, which performs the data processing in relation to the flare measurement, is connected to the main control system 31.

During the exposure, the wafer W is arranged in a partition 7 so that a gas, which is generated from the resist on the wafer W, does not exert any harmful influence on the mirrors M1 to M6 of the projection optical system PO. An opening, through which the exposure light EL is allowed to pass, is formed in the partition 7. The space in the partition 7 is vacuum-evacuated by a vacuum pump (not shown) under the control of the main control system 31.

When one shot area (die) on the wafer W is exposed, the circular arc-shaped illumination area 27R is formed on the reticle RC by the illumination optical system ILS, and the reticle RC and the wafer W are synchronously moved (subjected to the synchronous scanning) with respect to the projection optical system PO in the Y direction at a predetermined velocity ratio in accordance with the reduction magnification of the projection optical system PO. In this way, one die on the wafer W is exposed with the reticle pattern. After that, the wafer W is step-moved in the X direction and the Y direction by driving the wafer stage WST, and then the next shot area on the wafer W is subjected to the scanning exposure with the pattern of the reticle RC. In this way, the plurality of shot areas on the wafer W are successively exposed with the image of the pattern of the reticle RC in the step-and-scan manner.

Next, an explanation will be made about the flare of the projection optical system PO of this embodiment. The scattered light, which is the factor or main cause of the flare of the projection optical system PO, results from the surface roughness of each of the mirrors M1 to M6. The magnitude or degree of the flare correlates with the surface roughness PSD (Power Spectrum Density) which is the function of the power spectrum density exhibiting the magnitude or degree of the surface roughness, i.e., the function which relates to the magnitude or degree of the roughness with respect to the in-plane spatial frequency of the mirror. In particular, when the scattering angle is small, the surface roughness PSD has a same shape as that of the flare PSF (Point Spread Function) which is the point intensity spread function brought about by the flare. The surface shape is two-dimensional. Therefore, PSD is originally two-dimensional as well. However, in a case that the anisotropy is not taken into consideration, the rotational average is derived for those having the same frequency to be dealt with as "radial PSD".

The surface roughness radial PSD is in inverse proportion to the square of the spatial frequency f with a proportional coefficient k, as follows.

$$\text{radial } PSD(f) \approx k \cdot f^{-2} \qquad (1)$$

When the logarithms (log) of the both sides are taken, the following expression is obtained.

$$\log(\text{radial } PSD(f)) \approx -2 \cdot \log f + \log k \qquad (2)$$

Figure 5A:
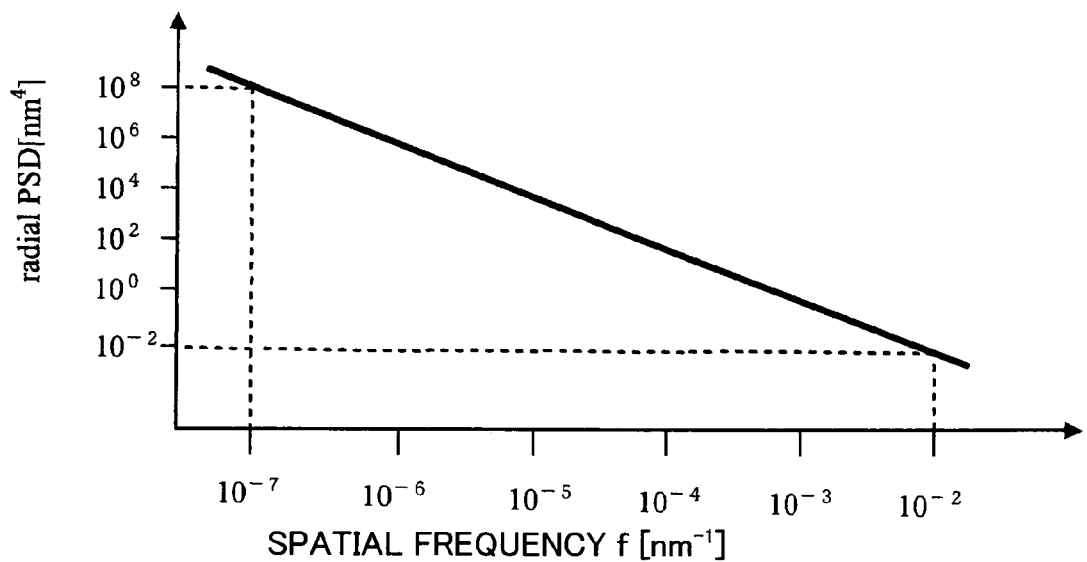
FIG. 5A shows an example of a Power Spectrum Density (PSD) in the radial direction of the roughness of a mirror surface.

In this way, the radial PSD of the surface roughness is expressed by a straight line having an inclination or slope of −2 in the log scale. This is referred to as "fractal straight line". The actual surface shape is not ideal, and hence it is not coincident with the fractal straight line which is in inverse proportion to the square. However, it is empirically known that the approximation can be made for a good or satisfactory polished surface with the function which is in inverse proportion to the square in a wide spatial frequency range. FIG. 5A shows an example of the fractal straight line of the radial PSD [$nm^4$] of the surface roughness. The horizontal axis in FIG. 5A is the spatial frequency f [$nm^{-1}$].

When all of the roughnesses of the optical surfaces as described above are totalized in the projection optical system PO, it is possible to estimate the effective surface roughness possessed by the projection optical system PO (if the surfaces are dealt with as a single surface). The effective surface roughness PSDs is expressed by the following sum of products.

$$PSDs(f) = \Sigma \alpha i \times PSDi(\alpha i \cdot fi) \quad (3)$$

In the expression, i represents the number of the optical surface (mirror), PSDi represents the radial PSD of the ith mirror, fi represents the spatial frequency in relation to the ith mirror, and αi represents the value of the ratio of the pupil diameter with respect to the diameter of an area in which the pupil diameter is projected onto the ith mirror. In accordance with the totalization as described above, the surface roughnesses of the respective mirrors are projected and superimposed on the pupil plane while being appropriately magnified and/or reduced, and the result is equivalent to that obtained if an optical system, in which the resultant roughness exists on the pupil plane, is virtually assumed.

When the PSDs (f) is used, the flare PSF (r), which results from the surface roughness, is expressed by the following expression.

$$PSF(r) = (4\pi/(\lambda^2 z))^2 \cdot PSDs(r/(\lambda z)) \quad (4)$$

In the expression, r represents the distance on the wafer (distance of arrival of the scattered light), λ represents the wavelength, and z represents the optical height of the pupil. PSD, which is the basis of the calculation, is the radial PSD. Therefore, the flare PSF is the rotationally symmetric radial PSF as well. As also appreciated from the introduction of the expression, all of the processes of calculation from PSD to PSF are coupled or correlated by the linear transformation. Therefore, the surface roughness PSD and the flare PSF have a same shape under the predetermined approximation. This fact is described, for example, in a reference "Christof Krautschik, et al.: Proceedings of SPIE, (United States) Vol. 4688, p. 289 (2002)".

Figure 5B:
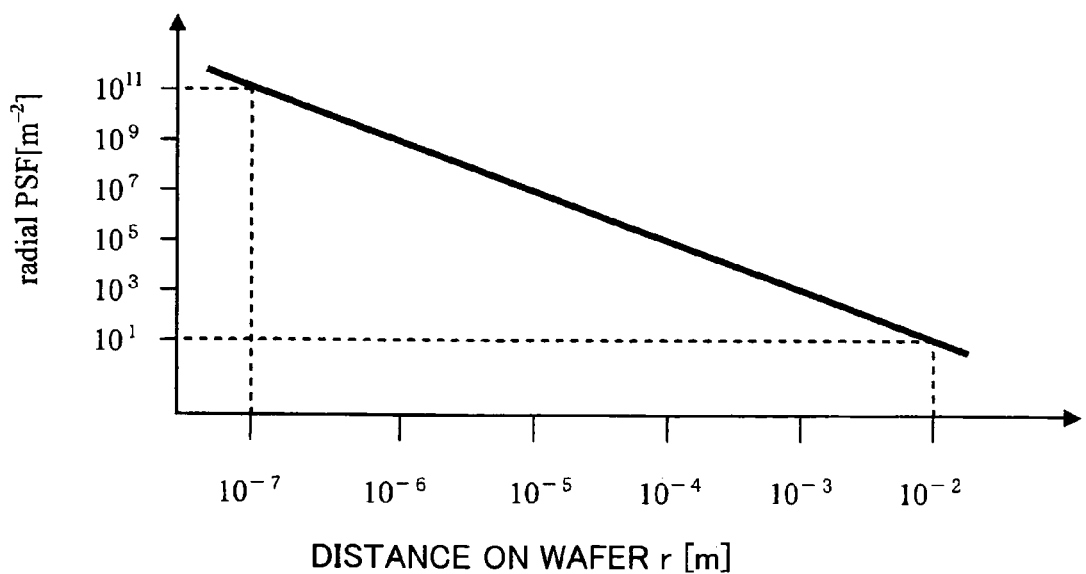
FIG. 5B shows an example of a Point Spread Function (PSF) in the radial direction of the flare of the projection optical system.

FIG. 5B shows an example of the radial PSF [m$^{-2}$] of the flare. In FIG. 5B, the horizontal axis is the distance r [m] on the wafer.

The physical origin of the flare PSF is the surface roughness PSD. The surface roughness PSD has such a feature that the approximation can be made by the fractal straight line which is in inverse proportion to the square of the spatial frequency f in the case of the radial PSD. Therefore, it is appropriate that the anisotropy of PSD is considered in each of the orientations based on the degree of the deviation from the function which is in inverse proportion to the square of the spatial frequency f, i.e., PSD is considered on the f-θ coordinate system (polar coordinate system of the angle θ). In other words, it is appropriate that the flare PSF is considered on the r-θ coordinate system (polar coordinate system of the angle θ) as well. When the flare light is estimated, it is extremely easy to integrate the flare PSF on the polar coordinate system as compared with a case in which the flare PSF is integrated on the x-y coordinate system (rectangular coordinates system).

In view of the above, in this embodiment, the evaluating pattern for the flare is also based on the r-θ coordinate system, because the roughness PSD is originally based on the f-θ coordinate system, and the flare PSF is based on the r-θ coordinate system.

That is, when the flare of the projection optical system PO is measured, the test reticle RT shown in FIG. 2A is loaded on the reticle stage RST shown in FIG. 1, instead of the reticle RC. The test reticle RT is produced by forming a reflective layer made of Mo/Si-multilayer film, etc. on a substrate made of a material through which the exposure light is transmissive, for example, silica glass, low-thermal expansion glass, etc., and forming an absorbing layer PAB, for example tantalum nitride (TaN), tantalum germanium nitride (TaGeN), etc. which absorbs the exposure light on the reflective layer. The absorbing layer PAB defines an evaluating pattern with a part or parts (portion or portions) of the absorbing layer being removed with a predetermined pattern, as will be described later on.

As shown by a bottom view in FIG. 2A, three arrays of evaluating pattern-forming portions 37A, 37B, 37C are set at predetermined intervals in the X direction on the pattern area PA of the test reticle RT. Six evaluating patterns 4A, 4B, 4C, 4D, 4E, 4F, which have a same shape and which have or are oriented in different directions, are formed at intervals L in the Y direction (in a scanning direction SD or in a movement direction) respectively, in each of the evaluating pattern-forming portions 37A to 37C. The spacing distances between the centers of the evaluating patterns 4A to 4F of the adjacent evaluating pattern-forming portions 37A to 37C are not less than L. In a case that the outer diameter of each of the evaluating patterns 4A to 4F is about several 10 μm, the lower limit value of the distance L (details will be described later on) is decreased in accordance therewith. Therefore, the evaluating patterns 4A to 4F may be arranged while being separated from each other approximately by the lower limit value of the distance L, for example, in two arrays in the vicinity of a position approximately regarded as the same evaluation point in the pattern area PA.

Each of the evaluating patterns 4A to 4F is formed by a reflective layer having a predetermined pattern which is formed by removing a part or parts of the absorbing layer PAB with the predetermined pattern and which is exposed in the absorbing layer PAB, and each of the evaluating patterns 4A to 4F has a size accommodated in at least the width in the Y direction of the illumination area 27R. In ordinary cases, a plurality of the evaluating patterns (any one of 4A to 4F) can be arranged within the width in the Y direction of the illumination area 27R. In this embodiment, the illumination area 27R is circular arc-shaped. For example, the position of the central evaluating pattern-forming portion 37B is shifted or deviated in the Y direction so that the evaluating patterns (for example, 4A), which are directed in the same direction in the respective evaluating pattern-forming portions 37A to 37C (or a plurality of the evaluating patterns included in the same arrangement), are simultaneously included in the illumination area 27R. Three or more arrays (for example, five arrays) of the evaluating pattern-forming portions may be provided in the pattern area PA. In a case that the evaluating patterns 4A to 4F are collectively arranged in the vicinity of the position which can be regarded as substantially the same evaluation point, sets of evaluating patterns having shapes different from those of the evaluating patterns 4A to 4F may be arranged in the Y direction of the evaluating pattern-forming portions 37A to 37C.

Figure 2B:
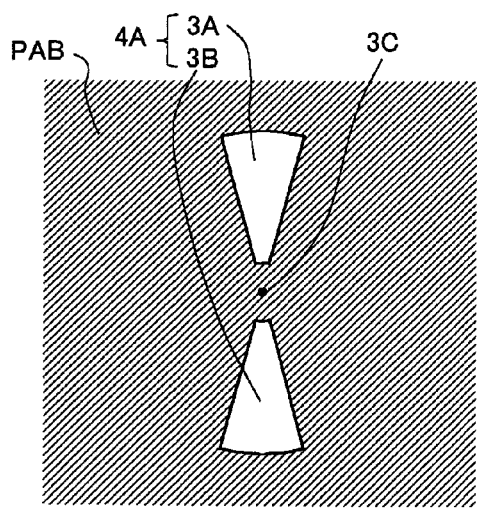
FIG. 2B is a magnified view of the evaluating pattern shown in FIG. 2A.
Figure 2C:
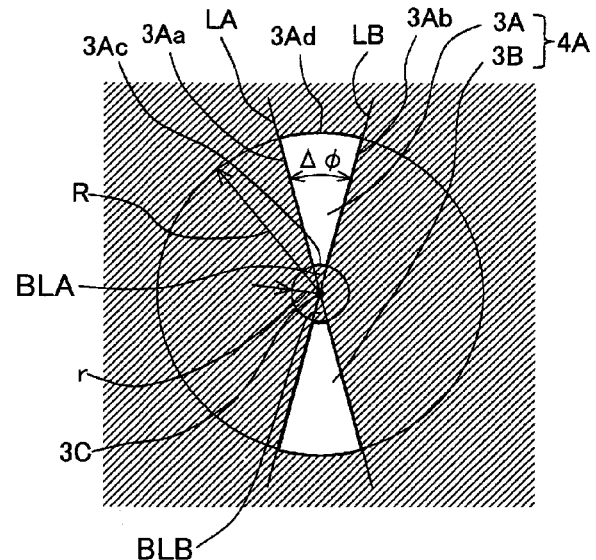
FIG. 2C is a magnified view to illustrate the shapes of sectoral patterns constructing the evaluating pattern.

As shown in a magnified view in FIG. 2B, one evaluating pattern 4A shown in FIG. 2A has a pair of sectoral patterns 3B-3A and 3B which have a same shape and which are arranged symmetrically in relation to a central point 3C which serves as the rotational center. As shown in FIG. 2C, it is assumed that two straight lines LA, LB intersect with each other at an angle Δφ on the central point 3C. On this assumption, the one sectoral pattern (first area) 3A is a reflective pattern surrounded by a first side 3Aa and a second side 3Ab which are disposed on the straight lines LA, LB, an inner diameter portion 3Ac which is disposed on a circumference having a radius r connecting ends (first ends), of the first side 3Aa and the second side 3Ab, disposed on the side of the central point 3C, and an outer diameter portion 3Ad which is disposed on a circumference having a radius R (>r) connecting ends, of the first side 3Aa and the second side 3Ab, disposed on the outer side (second ends, of the first side 3Aa and the second side 3Ab, having a wider spacing distance therebetween than a spacing distance between the ends of the first side 3Aa and the second side 3Ab disposed on the side of the central point 3C, when the spacing distances between the both ends of the first side 3Aa and the second side 3Ab are compared with each other). In other words, the sectoral pattern 3A is a sectoral reflective pattern which is formed in the absorbing layer PAB and which has the opening angle of $\Delta\phi$, the inner radius of r, and the outer radius of R. The sectoral pattern 3A can be considered as an area which is extended from the central point 3C in the radial direction from a position of distance r (the position away from the central point 3C by the distance r) to a position of distance R (the position away from the central point 3C by the distance R) and which is spread about the central point 3C at the opening angle $\Delta\phi$. On the other hand, the other sectoral pattern (second area) 3B is the identical pattern to the sectoral pattern 3A (symmetrical pattern to the sectoral pattern 3A with respect to the central point 3C) which is obtained by rotating the sectoral pattern 3A by 180° about the central point 3C. Therefore, the pair of sectoral patterns 3A, 3B can be also expressed as the pattern obtained by extracting the portions interposed between the two straight lines LA, LB from the bow tie-shaped pattern or the annular or zonal pattern. An area (block area) which includes the central point 3C exists between the pair of sectoral patterns 3A and 3B. In particular, small sectoral areas BLA and BLB are defined by the inner diameter portion 3Ac disposed on the circumference on the radius r and the two straight lines LA and LB.

For example, in a case that the opening angle $\Delta\phi$ is small, the inner diameter portion 3Ac (as well as the outer diameter portion 3Ad) can be approximated by a straight line as well.

The opening angle $\Delta\phi$ of each of the sectoral patterns 3A, 3B is, for example, 30°. In this case, the other evaluating patterns 4B, 4C, 4D, 4E, 4F shown in FIG. 2A are obtained by rotating the pattern having the same shape as that of the evaluating pattern 4A (sectoral patterns 3A, 3B) about the central point by 30° (=$\Delta\phi$), 60° (=2·$\Delta\phi$), 90° (=3·$\Delta\phi$), 120° (=4·$\Delta\phi$), and 150° (=5·$\Delta\phi$) respectively. Accordingly, the evaluating patterns 4A to 4F are arranged without any angle areas (angle ranges) overlapping with each other and without any gap in all of the orientations. Namely, although the evaluating patterns 4A to 4F have the same opening angle $\Delta\phi$, the evaluating patterns 4A to 4F are directed or oriented in the different directions respectively (the first side 3Aa and the second side 3Ab are extended in different directions among the evaluating patterns 4A to 4F). Further, the total of the opening angles $\Delta\phi$ of the evaluating patterns 4A to 4F is 360°.

Each of the opening angles $\Delta\phi$ of the pair of sectoral patterns 3A, 3B constructing the evaluating pattern 4A may be, for example, 180°/m or the supplementary angle thereof (=180°−180°/m) by using an integer m of not less than 2.

$$\Delta\phi = 180°/m \text{ or } -180°/m \tag{5}$$

In this case, those usable as the other evaluating patterns include m (m pairs of) evaluating patterns in which the sectoral patterns 3A, 3B having the opening angles $\Delta\phi$ are arranged in orientations which are different from each other by $\Delta\phi$.

The spatial frequency f of the surface roughness PSD corresponds to the distance r of the r-$\theta$ coordinate system of the flare PSF in relation to the radius r of the inner diameter portion 3Ac and the radius R of the outer diameter portion 3Ad of each of the sectoral patterns 3A, 3B. As shown in FIG. 5A, the spatial frequency f and the radial PSD are in the relationship represented by the straight line in the log scale. Therefore, it is most effective to equally divide the spatial frequency f in the log scale. In other words, it is also effective to equally divide the inner diameter or radius and the outer diameter or radius of the actual pattern in the log scale. For example, it is assumed that the minimum distance of the inner radius r is 1 µl and the maximum distance of the outer radius R is 1 mm at the stage of the images of the sectoral patterns 3A, 3B brought about by the projection optical system PO. On this assumption, the range has three digits. For example, the sectoral patterns 3A, 3B having various shapes, which have radii r and R obtained by equally dividing the same appropriately in the log scale, may be formed beforehand in the pattern area PA of the test reticle RT shown in FIG. 2A. Alternatively, such sectoral patterns may be formed beforehand while being separated into those disposed on a plurality of test reticles.

For example, when one digit is equally divided into four, a series of values of the respective radii r, R to be prepared are, for example, 1 µm, 1.8 µm, 3.2 µm, 5.6 µm, 10 µm, 18 µm, 32 µm, 56 µm, 100 µm, 180 µm, 320 µm, 560 µm, and 1 mm. When the sets of radii r, R, which have the sizes or dimensions as described above and in which r<R is given, are selected, the band or zone of the spatial frequency f can be provided substantially equally in the log scale.

Further, the minimum value of the distance L between the centers of the evaluating patterns 4A to 4F shown in FIG. 2A is determined in order to perform the flare evaluation at a necessary evaluation accuracy by the following method. It is assumed that the inner radius r is represented by a×R (a<1), the center-to-center distance L is represented by p×R (p>1), the number of the evaluating patterns 4A to 4F to be arranged therearound is N, and the maximum allowable value of the relative error of the evaluation is e, by using the outer radius R of each of the sectoral patterns 3A, 3B of the adjacent evaluating patterns 4A, 4B shown in FIG. 2A. On this, assumption, the relative error can be made to be not more than e, provided that the spacing distance L (=p×R) between the evaluating patterns is increased to effect the separation so that the parameter p is approximately in the following range.

$$p > \sqrt{\{N \times (a^2-1)/(1.98 \times e \times \ln a)\}} \tag{6}$$

When this relationship is used, if an adjacent evaluating pattern adjacent to a certain evaluating pattern is of the same type (having the same opening angle) as that of the certain pattern, and the adjacent evaluating pattern has any different size, then the relative error can be made to be not more than e when the evaluating patterns are separated from each other so that the parameter p is approximately in the following range, for example, by using the outer radius R of the certain evaluating pattern (sectoral patterns 3A, 3B), assuming that the inner radius r is a×R (a<1), the outer radius R' of the adjacent evaluating pattern is c×R, the inner radius r' is b×(c×R), the center-to-center distance L' with respect to the adjacent evaluating pattern is p×R (p>1), the number of the evaluating patterns to be arranged therearound is N, and the maximum allowable value of the relative error of the evaluation is e.

$$p > c^2 \times \sqrt{\{N \times (b^2-1)/(1.98 \times e \times \ln a)\}} \tag{7}$$

In a case that any large evaluating pattern is arranged at any farther position, it is necessary to slightly widen the spacing distance in consideration of this fact as well. The foregoing parameter p can be approximately calculated as follows.

It is now assumed that the inner radius r is a×R, the center-to-center distance L with respect to the adjacent evaluating pattern is p×R, and the number of the adjacent evaluating patterns is N, by using the outer radius R of the evaluating pattern (sectoral patterns 3A, 3B). It is now assumed that the evaluating pattern is not the evaluating patterns 4A to 4F of this embodiment, but the evaluating pattern is a conventionally used annular pattern. Further, it is assumed that the flare PSF is generally represented as follows by using a coefficient k.

$$PSF(r) = k \times r^{-2} \qquad (8)$$

On this assumption, the flare amount F0, which is brought about by the evaluating pattern itself, is as follows.

$$F0 = 2\pi k \times \ln(R/r) = 2\pi k \times \ln a \qquad (9)$$

The flare amount F from the surrounding pattern is approximately as follows.

$$F = N \times \beta \times 2\pi k \times \ln((L+R)/(L-R)) \qquad (10)$$

In the expression, β represents the ratio of the area occupied by one corresponding to one adjacent evaluating pattern in the annular area ranging from the radius (L−R) to the radius (L+R), which is expressed as follows.

$$\beta = \pi(R^2 - r^2)/[\pi\{(L+R)^2 - (L-R)^2\}] \qquad (11)$$

On this condition, assuming that the allowable error e=F/F0 is given, the expressions (9) and (10) are applied thereto to obtain the following relationship.

$$(1/p)\ln((p+1)/(p-1)) = 4 \times e \times R^2 \times \ln a/\{N \times (R^2 - r^2)\} \qquad (12)$$

It is affirmed that any case, in which a large error of not less than 20% is permitted as the relative error, is ordinarily absent. Therefore, the left side of the expression (12) can be dealt with as the straight line approximation on the log scale approximately in a range of e<0.2. The expression (12) can be approximated as follows. The expression (6) is derived from the following expression.

$$p^2 e/N = -0.505(1-a^2)/\ln a \approx (a^2-1)/(1.98 \times \ln a) \qquad (13)$$

The above calculation is the case in which the adjacent evaluating pattern is of the same type as that of the certain pattern. However, even in a case of any different type, the foregoing expression (7) can be derived in accordance with the same or equivalent calculation. Even when the certain pattern is the sectoral pattern 3A, 3B as in this embodiment, if the opening angle of the certain pattern is the same as that of the adjacent pattern, then the same area ratio is provided. Therefore, it is possible to use the same expression. If the opening angle of the certain pattern is different from that of the adjacent pattern, the adjustment may be made in relation to the expression by using the number N of the surrounding evaluating pattern or patterns.

According to the above, for example, in a case that it is intended to suppress the relative error to be not more than 1 (e=0.01), if eight pieces of identical evaluating patterns are arranged around the certain evaluating pattern, then p>15.5 is given assuming that the value of the ratio a=r/R=0.2 is given between the inner radius and the outer radius of the sectoral pattern 3A, 3B (for example, r is 2 μm and R is 10 μm). Therefore, the center-to-center distance L with respect to the adjacent evaluating pattern, which should be adopted, is not less than 155 μm which is 15.5 times the outer radius R of the pattern (7.7 times the outer diameter of the pattern). The area, which is disposed therebetween, is the exclusive area in which any evaluating pattern (reflective pattern) should not be arranged. If the evaluating pattern is arranged nearer to the above, there is such a possibility that the relative error cannot be suppressed to be not more than 1%.

In relation to the evaluation of the anisotropy of the flare on a certain image point evaluated as described above, it is necessary to pay attention to the fact that the flare PSF corresponding to the image point does not have the evaluated anisotropy. The flare is the amount of the irradiation of the flare PSF on another image point onto the certain image point separated therefrom by a certain distance in a certain orientation. Therefore, the anisotropy of the flare, which is observed at a certain image point, merely is the observation of the difference in the flare light arrived from another image point over a predetermined distance at a predetermined angle. Therefore, in a case that the flare PSF at a certain image point is compared with the calculation result, it is necessary to recombine the data based on the evaluation results of the flare anisotropy in relation to a large number of image points in a large number of orientations.

It is assumed that the opening angle Δϕ is 30°, the radius r in the state of the projected image is 1 μm, and the radius R is 5.6 μm in the state of the projected image in relation to the pair of sectoral patterns 3A, 3B of the evaluating pattern 4A shown in FIG. 2C. On this assumption, it is possible to evaluate at the measuring point 39A of the exposure area 27W on the wafer shown in FIG. 4D, without any excess and any shortage, the flare in the range ranging from the distance 1 μm to the distance 5.6 μm within each of the angle ranges 40A, 41A of ±15° about the center of the X axis. Similarly, by using the evaluating patterns 4B to 4F having the different orientations included in the evaluating pattern-forming portion 37A shown in FIG. 2A, it is possible to evaluate at the measuring point 39A shown in FIG. 4D, without any excess and any shortage, the flare in the range ranging from the distance 1 μm to the distance 5.6 μm within each of the corresponding angle ranges 40B to 40F and 41B to 41F respectively. Therefore, it is possible to measure the flares in all of the directions without any oversight or omission. Similarly, it is possible to measure the flares in all of the directions without any oversight or omission, and it is possible to correctly evaluate the anisotropy of the flare based on the difference in the flare in each of the orientations at the other measuring points 39B, 39C shown in FIG. 4D by using the evaluating patterns 4A to 4F included in the other evaluating pattern-forming portions 37B, 37C shown in FIG. 2A.

With reference to FIG. 2A, it is assumed that other five evaluating patterns are present at the maximum around the evaluating patterns 4A to 4F. On this assumption, the parameter p is larger than 11.9 according to the expression (6). Therefore, it is appropriate that the distance L between the centers of the evaluating patterns is increased to make separation by larger than 60 μm in the state of the projected image. Further, when a slight safety factor is taken into consideration, then the center-to-center distance is increased to make separation by 65 μm, and any reflective pattern may not be arranged therebetween at all.

The center-to-center distance L of the pattern, which is required, for example, when the radius r of the sectoral pattern 3A, 3B is 1 μm and the radius R is 100 μm, is p>7.4 according to the expression (6) assuming that the allowable relative error is 1% and the number of evaluating patterns arranged therearound is 5. Therefore, the center-to-center distance may be increased to make separation by larger than 740 μm in the state of the projected image.

Figure 3A:
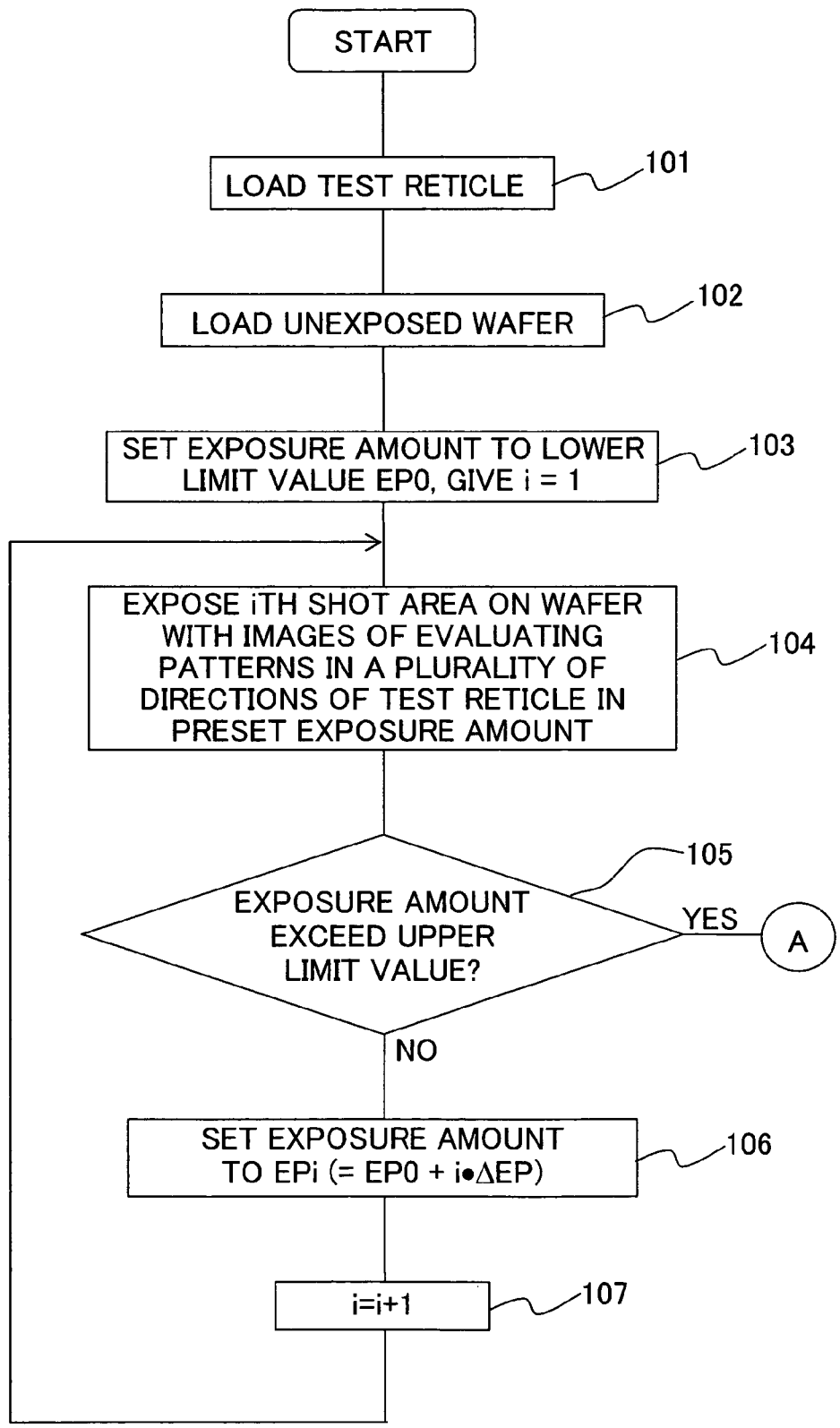
FIGS. 3A and 3B show a flow chart illustrating an exemplary operation for measuring the flare of a projection optical system and correcting a pattern of a reticle based on an obtained measurement result.
Figure 3B:
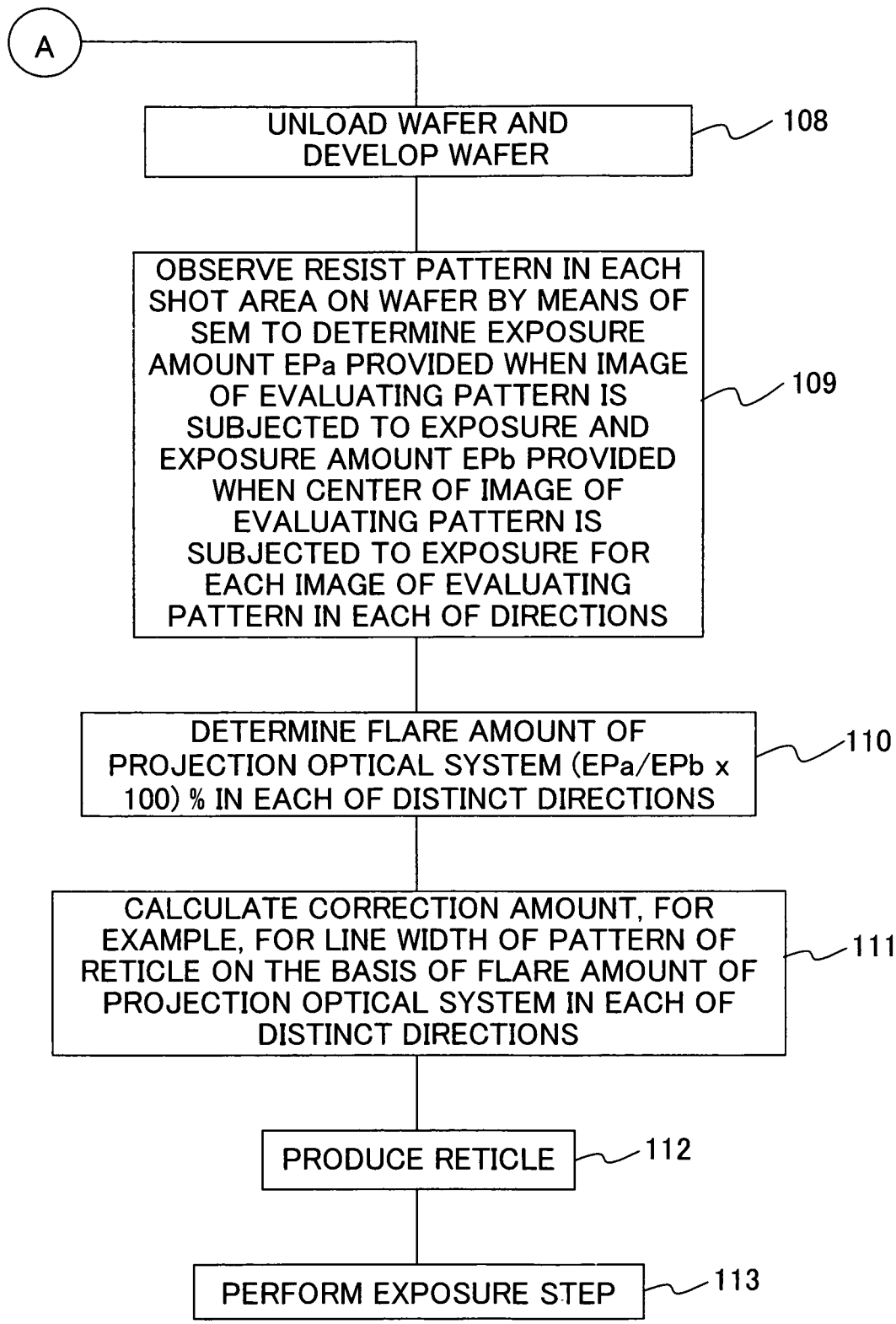

Next, an explanation will be made with reference to a flow chart shown in FIGS. 3A and 3B about an example of the operation for evaluating the flare of the projection optical system PO of the exposure apparatus 100 by using the test reticle RT shown in FIG. 2A. In this procedure, the operation of the exposure apparatus 100 is controlled by the main control system 31. At first, in Step 101 shown in FIG. 3A, the test reticle RT shown in FIG. 2A is loaded on the reticle stage RST shown in FIG. 1; and the alignment is performed for the test reticle RT by using an alignment mark (not shown) of the test reticle RT. Subsequently, in Step 102, an unexposed wafer (referred to as "W"), which is coated with a positive type resist, is loaded on the wafer stage WST. Subsequently, in Step 103, the main control system 31 sets the exposure amount of the wafer to a predetermined lower limit value EP0 which is lower than the photosensitive level of the resist, and 1 is given for the value of the control parameter i. Subsequently, in Step 104, the exposure apparatus 100 is used to expose a certain shot area 38A on the wafer W shown in FIG. 4A with images of the evaluating patterns 4A to 4F in the plurality of directions included in the evaluating pattern-forming portions 37A to 37C of the test reticle RT, in the preset exposure amount EP0. In this procedure, as shown in FIG. 2A, each of the portions of the pattern of the test reticle RT, which is illuminated with the illumination area 27R, is subjected to the exposure in the preset exposure amount in the step-and-repeat manner. For example, the images of the evaluating patterns 4A to 4F, which are included in each of the evaluating pattern-forming portions 37A to 37C, are subjected to the exposure in the vicinity of the predetermined measuring points 39A to 39C of the exposure area 27W shown in FIG. 4D respectively.

The images 4AP to 4FP of the evaluating patterns 4A to 4F are exposed on areas 37AP to 37CP, which correspond to the evaluating pattern-forming portions 37A to 37C on the shot area 38A on the wafer W shown in FIG. 4A, in the Y direction respectively. Each of the images 4AP to 4FP is formed by images 3AP, 3BP of one of the pair of sectoral patterns 3A, 3B. However, for the convenience of explanation, it is assumed that the images of the patterns of the test reticle RT, which are erecting in the X direction and the Y direction, are formed on the wafer W. FIG. 2A shows the bottom view illustrating the test reticle RT, and FIG. 4A is the plan view illustrating the wafer W. Therefore, the both are subjected to the inversion in the X direction.

Subsequently, in Step 105, it is judged whether or not the preset exposure amount arrives at the predetermined upper limit value (value higher than the level at which the resist is expected to be exposed with the flare). At this stage, the exposure amount does not arrive at the upper limit value. Therefore, the operation proceeds to Step 106, and the main control system 31 increases the exposure amount of the wafer by a predetermined amount ΔEP based on the following expression. The predetermined amount ΔEP is set depending on the measurement accuracy for the flare.

$$EPi=EP0+i \cdot \Delta EP \tag{14}$$

After that, 1 is added to the value of the parameter i in Step 107, and then the ith shot area 38B (in this case, i=2) on the wafer W is exposed with the images of the plurality of arrays of the evaluating patterns 4A to 4F of the test reticle RT in the set exposure amount EPi. The information about the set exposure amount EPI on the wafer W and the sequence (position) of the corresponding shot area is stored in the data processing system 36. After that, for example, shot areas 38C, 38D on the wafer W shown in FIG. 4A are exposed with the images of the plurality of arrays of the evaluating patterns 4A to 4F of the test reticle RT in the gradually increasing exposure amount EPi respectively until the set exposure amount EPi exceeds the upper limit value thereof. The three arrays of the areas 37AP to 37CP of the shot areas 38B to 38D and other shot areas (not shown) on the wafer W are also exposed with the images 4AP to 4FP of the evaluating patterns 4A to 4F respectively. If one wafer is insufficient for a number of the shot areas to be subjected to the exposure, a large number of the shot areas disposed on a plurality of wafers may be exposed with the images of the patterns of the test reticle RT in the gradually increasing exposure amount.

After that, if the set exposure amount EPi exceeds the upper limit value, the operation proceeds from Step 105 to Step 108; and the wafer W is unloaded from the exposure apparatus 100, and the wafer W is transported to an unillustrated coater/developer. The resist of the wafer W is developed by the coater/developer. The resist pattern is formed by eliminating (dissolving) the portions corresponding to the images 4AP to 4FP of the evaluating patterns 4A to 4F shown in FIG. 4A, for example, in each of the shot areas 38A to 38D on the wafer W after the development.

Subsequently, in Step 109, the wafer W after the development is set in an unillustrated scanning electron microscope (SEM) to determine information about the sequence of the shot areas provided when the genuine image portions are exposed (eliminated) and information about the sequence of the shot areas provided when the centers of the images 4AP to 4FP (images of the central points 3C) are exposed (eliminated) for each of the images 4AP to 4FP of the evaluating patterns 4A to 4F in the respective directions and for each of the areas 37AP to 37CP of, for example, all of the shot areas 38A to 38D subjected to the exposure on the wafer W shown in FIG. 4A. These informations are supplied to the data processing system 36 shown in FIG. 1.

In this procedure, the case in which the genuine image of the evaluating pattern 4A is representatively subjected to the exposure means that the recessed resist patterns 3AP, 3BP are formed at the positions of genuine images 3AR, 3BR of the pair of sectoral patterns 3A, 3B constructing the evaluating pattern 4A as shown in FIG. 4B. On the other hand, the case in which the center of the image 4AP of the evaluating pattern 4A is subjected to the exposure means that the resist patterns 3AR, 3BR, which correspond to the images 3AP, 3BP of the sectoral patterns 3A, 3B, are gradually widened due to the flare, and the resist patterns 3AR, 3BR are connected to each other at the portion of an image 3CP of the central point 3C of the sectoral patterns 3A, 3B as shown in FIG. 4C. Note that in the case that the resist patterns 3AR, 3BR are connected to each other at the portion of the image 3CP of the central point 3C of the sectoral patterns 3A, 3B, the image of the areas (block areas) BLA, BLB which are interposed between or sandwiched by the sectoral patterns 3A, 3B of the evaluating pattern 4A does not appear, as shown in FIG. 4C. In such a case, it is not necessary that the images of the resist patterns 3AR, 3BR maintain the sectral shapes as shown in FIG. 4C; and the images of the resist patterns 3AR, 3BR may be connected at the portion of the image 3CP of the central point 3C such that the images of the resist patterns 3AR, 3BR are widened as a whole. Namely, it is allowable that the resist patterns 3AR, 3BR are not formed to have the sectral shapes.

The data processing system 36 determines an exposure amount EPa provided when the portions of the genuine images are subjected to the exposure and an exposure amount EPb provided when the center of the images is subjected to the exposure due to the flare for each of the images 4AP to 4FP of the evaluating patterns 4A to 4F in the respective directions for each of the areas 37AP, 37CP, i.e., for each of the corresponding measuring points 39A to 39C in the exposure area 27W shown in FIG. 4D by using the information about the sequence (positions) of the shot areas and the information about the exposure amount EPi provided when each of the shot areas is subjected to the exposure. Subsequently, in Step 110, the data processing system 36 calculates a flare amount Fc of the projection optical system PO in accordance with the following expression for each of the evaluating patterns 4A to 4F and in each of the directions for each of the measuring points 39A to 39C. That is, the flare amount Fc is calculated based on the ratio (value of the ratio) of the exposure amount EPa with respect to the exposure amount EPb.

$$Fc=(EPa/EPb)\times 100(\%) \qquad (15)$$

Accordingly, the flare amount of the projection optical system PO is consequently measured without any gap in each of the six directions 40A, 41A to 40F, 41F for each of the measuring points 39A to 39C included in the exposure area 27W.

Subsequently, in Step 111, the data processing system 36 calculates the correction amount for the shape including, for example, the line width of the pattern of the reticle RC for the device shown in FIG. 1 based on the flare amount Fc in each of the directions of the projection optical system PO determined in Step 110.

Figure 6:
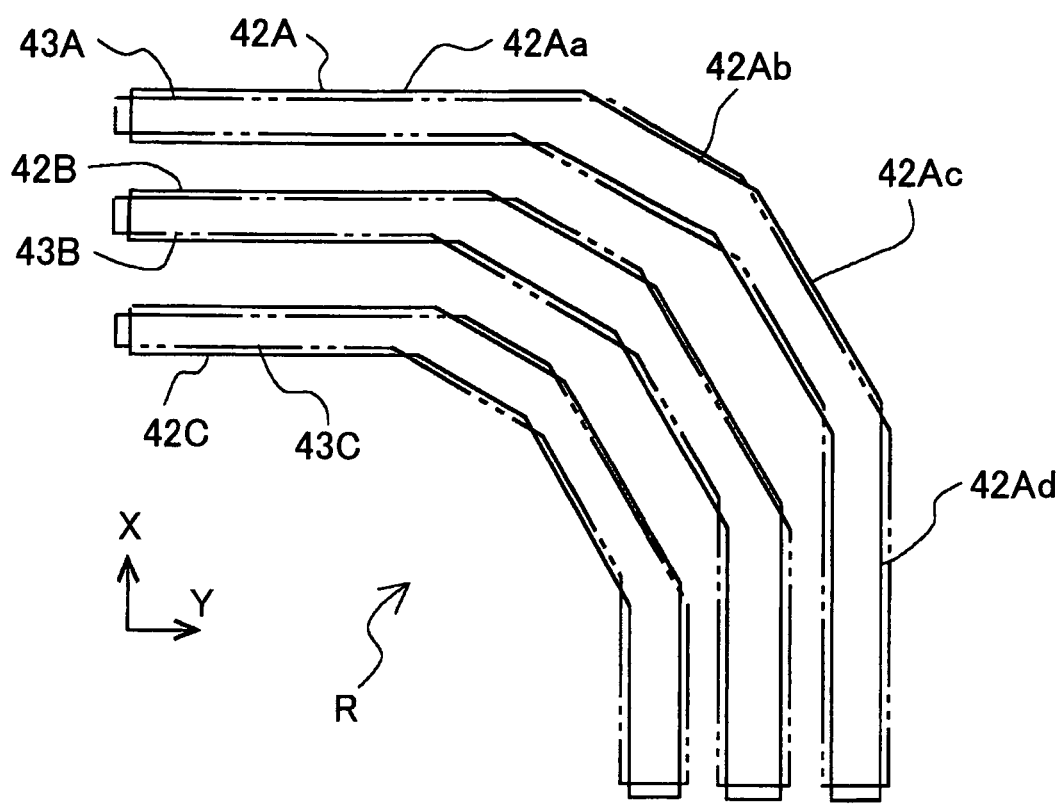
FIG. 6 is magnified plan view illustrating an exemplary pattern after the correction of the reticle.

For example, as shown in FIG. 6 in a magnified manner, it is assumed that parts of the pattern on the reticle R, which is provided when the flare of the projection optical system PO is not considered, are designated as circuit patterns 42A to 42C. On this assumption, for example, the correction amount for the line width or the like is calculated in order to form a pattern having the shape as exactly formed to follow the designed value on the wafer in consideration of the flare amount in the corresponding direction for each of portions 42Aa, 42Ab, 42Ac, 42Ad having different directions of the circuit pattern 42A. As a result, for example, circuit patterns 43A to 43C, which are depicted by two-dot chain lines, are obtained as circuit patterns after the correction.

After that, in Step 112, a reticle (patterning mask) (also referred to as "RC") is produced based on the correction amount obtained in Step 111. Subsequently, in Step 113, the reticle RC after the correction is loaded on the reticle stage RST shown in FIG. 1 to perform the exposure for the wafer W. Accordingly, it is possible to form the pattern as exactly shaped to follow the designed value on the wafer W, while correctly considering the flare in each of the distinct directions of the projection optical system PO.

The function, the effect, etc. of this embodiment are as follows.

(1) The method for measuring the flare of the projection optical system PO of the exposure apparatus 100 of this embodiment includes Step 101 of arranging, on the object plane of the projection optical system PO, the evaluating pattern 4A composed of the sectoral pattern 3A (aperture pattern) formed (surrounded) by the first side 3Aa, the second side 3Ab which is inclined at the angle Δϕ with respect to the first side 3Aa, and the inner diameter portion 3Ac and the outer diameter portion 3Ad which connect the both ends of the first side 3Aa and the both ends of the second side 3Ab, and the sectoral pattern 3B symmetrical to the sectoral pattern 3A; Step 104 of irradiating the exposure light onto the evaluating pattern 4A to project the image of the evaluating pattern 4A via the projection optical system PO; and Steps 109 and 110 of determining the flare information based on the ratio of the light amount of the exposure light irradiated onto the evaluating pattern 4A with respect to the light amount of the image of the evaluating pattern 4A provided via the projection optical system PO.

The conventional flare-measuring method, in which the pairs of bar-shaped patterns are arranged while being directed in the different directions, is such a method that the flare can be easily calculated on the rectangular coordinates system. However, the conventional flare-measuring method involves such a problem that the calculation is complicated on the polar coordinate system. In contrast to the conventional flare-measuring method, when the flare-measuring method of this embodiment is adopted, the flare information can be correctly measured within the range of the opening angle (predetermined angle) Δϕ of the sectoral patterns 3A, 3B constructing the evaluating pattern 4A by projecting the image of the evaluating pattern 4A. Further, if necessary, the measurement result can be easily processed on the polar coordinate system including, for example, the point intensity spread function PSF (Point Spread Function).

It is allowable that only the sectoral pattern 3A is arranged on the object plane of the projection optical system PO. In this case, it is possible to measure the flare in the direction of the sectoral pattern 3A.

(2) In this embodiment, the sectoral patterns 3A, 3B are symmetrical in relation to the central point 3C which is the point of intersection of the straight lines LA, LB obtained by extending the first side 3Aa and the second side 3Ab. Therefore, the flare can be easily evaluated by comparing the exposure amount provided at the position of the image of the central point 3C with the exposure amount provided at the positions of the images of the sectoral patterns 3A, 3B.

(3) In Step 102, the evaluating patterns 4B to 4F, each of which has the same shape as that of the evaluating pattern 4A and which are arranged in the different directions so that the angles are 360° in total, are also arranged. In Steps 108 to 110, the flare of the projection optical system PO is determined in each of the directions of the evaluating patterns 4A to 4F. Therefore, it is possible to measure the anisotropy of the flare of the projection optical system PO without any gap.

(4) The test reticle RT for measuring the flare of the embodiment described above is formed with the evaluating pattern 4A composed of the sectoral pattern 3A and the sectoral pattern 3B symmetrical thereto. Therefore, the flare-measuring method described above can be carried out by using the test reticle RT.

At least one of the inner diameter portion 3Ac and the outer diameter portion 3Ad of each of the sectoral patterns 3A, 3B may be a straight line irrelevant to the largeness/smallness of the opening angle.

The inner diameter portion 3Ac of each of the sectoral patterns 3A, 3B may be omitted, and the first side 3Aa and the second side 3Ab may directly intersect with each other. In this case, when the outer diameter portion 3Ad is a straight line, the sectoral patterns 3A, 3B can be dealt with as triangular patterns.

(5) The evaluating patterns 4A to 4F having the different directions are formed on the test reticle RT. Therefore, it is possible to measure the anisotropy of the flare of the projection optical system PO.

It is allowable that only one evaluating pattern 4A of the evaluating patterns 4A to 4F is formed beforehand on the test reticle RT shown in FIG. 2A. Alternatively, it is allowable that only two evaluating patterns (for example, 4A, 4B) of the evaluating patterns 4A to 4F are formed beforehand on the test reticle RT shown in FIG. 2A. Even in this case, it is possible to measure the flare in the direction of the evaluating pattern 4A (or in the directions of the evaluating patterns 4A, 4B).

It is also allowable that one sectoral pattern 3A of the evaluating pattern 4A is formed beforehand. Even in this case, it is possible to measure the flare in the direction of the sectoral pattern 3A.

(6) The test reticle RT has the reflective film which is provided on the surface of the substrate and which reflects the exposure light, and the absorptive film which is provided on the surface of the reflective film and which absorbs the exposure light. Each of the evaluating patterns 4A to 4F is formed as the reflective pattern obtained by removing a part of the absorptive film. Therefore, the test reticle RT can be used as the reflection type mask for the EUV exposure apparatus.

In this case, the substrate of the test reticle RT may be either a transmissive member through which the exposure light is transmitted or a metal member through which the exposure light is not transmitted.

In a case that the test reticle RT is used as the transmission type reticle for an exposure apparatus which uses an exposure light having a wavelength of, for example, 193 nm, the test reticle has, for example, a substrate through which the exposure light is transmissive, and a light shielding film which is provided on the surface of the substrate. The evaluating patterns, which correspond to the evaluating patterns 4A to 4F, are formed as transmissive patterns (aperture patterns) each obtained by removing a part of the light shielding film.

(7) The method for correcting the pattern of the reticle of this embodiment includes Steps 101 to 111 of measuring the flare information of the projection optical system PO by the flare-measuring method of this embodiment; and Step 112 of correcting the pattern based on the measurement result of the flare information. Therefore, the pattern of the reticle can be corrected while taking the anisotropy of the flare of the projection optical system PO into consideration as well.

(8) The exposure method of this embodiment is the exposure method for illuminating the pattern of the reticle RC with the exposure light EL and exposing the wafer W via the pattern and the projection optical system PO, which includes Steps 101 and 111 of measuring the flare information of the projection optical system PO by the flare-measuring method of this embodiment; Step 112 of correcting the pattern as the transfer objective based on the measurement result of the flare information; and Step 113 of exposing the wafer W via the pattern after the correction and the projection optical system PO. Therefore, even when the flare of the projection optical system PO is present, it is possible to form the target pattern on the wafer W.

Next, a modification of the foregoing embodiment will be explained with reference to FIG. 7 (FIGS. 7A to 7E).

Figure 7A:
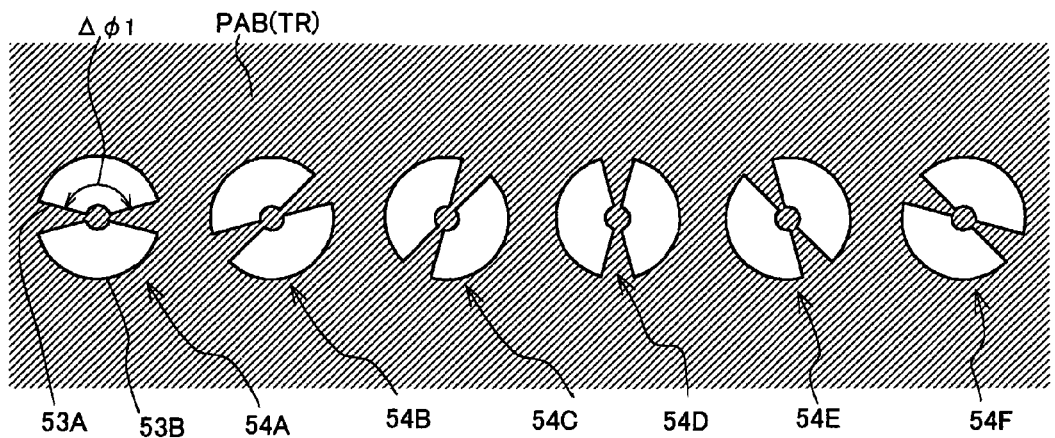
FIG. 7A is a magnified view illustrating a first modification of the evaluating pattern.

A test reticle TR shown in FIG. 7A has evaluating patterns 54A to 54F each of which is composed of a pair of sectoral patterns 53A, 53B having an opening angle $\Delta\phi1$ ($=180°-\Delta\phi$) as the supplementary angle as compared with each of the sectoral patterns 3A, 3B having the opening angle $\Delta\phi$ shown in FIG. 2A, the evaluating patterns 54A to 54F being arranged in an absorbing layer PAB while being rotated by the angle $\Delta\phi$. Assuming that the opening angle $\Delta\phi$ is 30°, the opening angle $\Delta\phi1$ of the sectoral pattern 53A, 53B is 150° which is five times the angle 30°. Therefore, the flare amount of the center of the images of the sectoral patterns 53A, 53B is five times the flare amount of the center of the images of the sectoral patterns 3A, 3B. It is possible to greatly narrow the variable range of the exposure amount. Therefore, it is possible to easily measure the flare amount.

An exposure amount, which is provided when the resist is exposed (eliminated) at the center of the images of the sectoral patterns 53A, 53B shown in FIG. 7A, is approximately equivalently about 6/5 of the exposure amount which is provided when the conventional annular pattern is used, wherein the flare is measured with ease. Further, the opening angle $\Delta\phi1$ of each of the sectoral patterns 53A, 53B is 150°, and the angle of the dark portion (absorbing layer PAB) disposed between the sectoral patterns 53A, 53B is 30°. Therefore, when the flare is evaluated by using the sectoral patterns 53A, 53B, it is possible to evaluate the flare in such a way that the influence of the flare, which is to be exerted in any orientation disposed therebetween, is excluded. Therefore, the measurement result of the flare, which is obtained when the evaluating patterns 4A to 4F shown in FIG. 2A are used, can be determined from the measurement result of the flares with the evaluating patterns 54A to 54F having the six orientations.

Figure 7B:
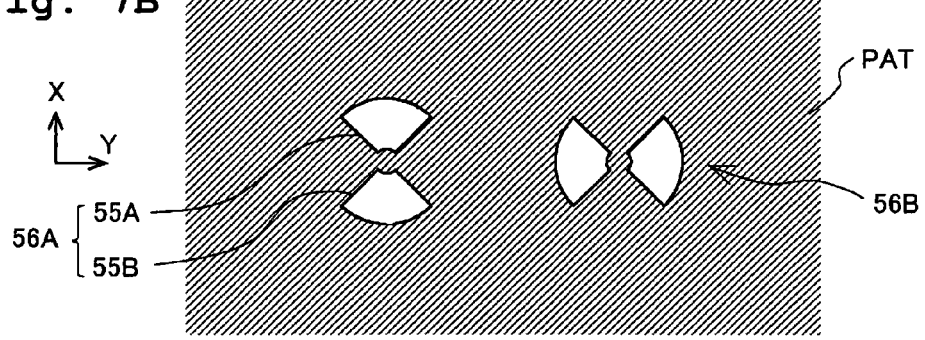
FIG. 7B is a magnified view illustrating a second modification of the evaluating pattern.

Another evaluating pattern for a transmission type reticle is shown in FIG. 7B, wherein it is also allowable to form, in a light shielding portion PAT, an evaluating pattern 56A which is composed of a pair of sectoral patterns 55A, 55B having an opening angle of 90°, and an evaluating pattern 56B which has such a shape that the evaluating pattern 56A is rotated by 90°.

Figure 7C:
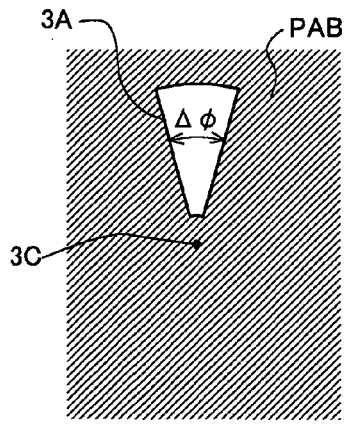
FIG. 7C is a magnified view illustrating a third modification of the evaluating pattern.
Figure 7D:
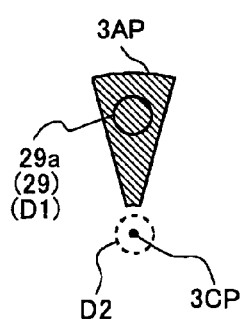
FIG. 7D shows an image of the pattern shown in FIG. 7C.

Still another evaluating pattern is shown in FIG. 7C; wherein only one sectoral pattern 3A having an opening angle $\theta\phi$ may be formed as a reflective layer in an absorbing layer PAB. In this case, it is assumed that the image of the sectoral pattern 3A, which is formed by the projection optical system PO, is an image 3AP shown in FIG. 7D. On this assumption, a light-receiving surface 29a of the irradiation amount monitor 29 shown in FIG. 1 may be firstly set at a position D1 of the center of the image 3AP to measure a light amount OP1, and then the light-receiving surface 29a may be moved to a position D2 which includes the image 3CP of the central point 3C of the sectoral pattern 3A to measure a light amount OP2. In this case, the flare amount in the direction of the image 3AP of the sectoral pattern 3A is OP2/OP1×100(%).

Figure 7E:
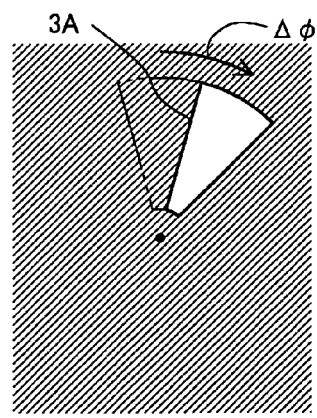
FIG. 7E shows a state that the pattern shown in FIG. 7C is rotated.

In this case, a rotatable table (not shown) is provided on the reticle stage RST shown in FIG. 1, and the flare amount is measured while rotating the sectoral pattern 3A by the angle $\Delta\phi$ respectively as shown in FIG. 7E. Accordingly, it is possible to measure the flare amount in all of the directions.

The sequence of the arrangement of, for example, the evaluating patterns 4A to 4F and 54A to 54F shown in FIGS. 2 and 7 is not limited to the arrangement explained in this embodiment.

The light shielding mechanism, which includes the light shielding plates 30Y1 and 30Y2 shown in FIG. 1 and the pair of light shielding plates in the X direction (not shown), may be omitted. By doing so, it is possible to measure the flare in a wide range not shielded by the light shielding plates 30Y1 and 30Y2 and the pair of light shielding plates in the X direction.

The embodiment shown in FIG. 1 is illustrative of the case in which the EUV light is used as the exposure light, and the all reflection projection optical system constructed of only the six mirrors is used. However, this case is provided by way of example. The present invention is also applicable, for example, to an exposure apparatus provided with a projection optical system constructed of, for example, only four mirrors as a matter of course as well as to an exposure apparatus provided with a projection optical system having, for example, four to eight mirrors while using the light source of a VW light source having a wavelength of 100 to 160 nm, for example, the $Ar_2$ laser (wavelength: 126 nm).

Further, the present invention is also applicable when a projection optical system, which is constructed of a dioptric system using, for example, an ArF excimer laser beam (wavelength: 193 nm) as the exposure light, is used.

Figure 8:
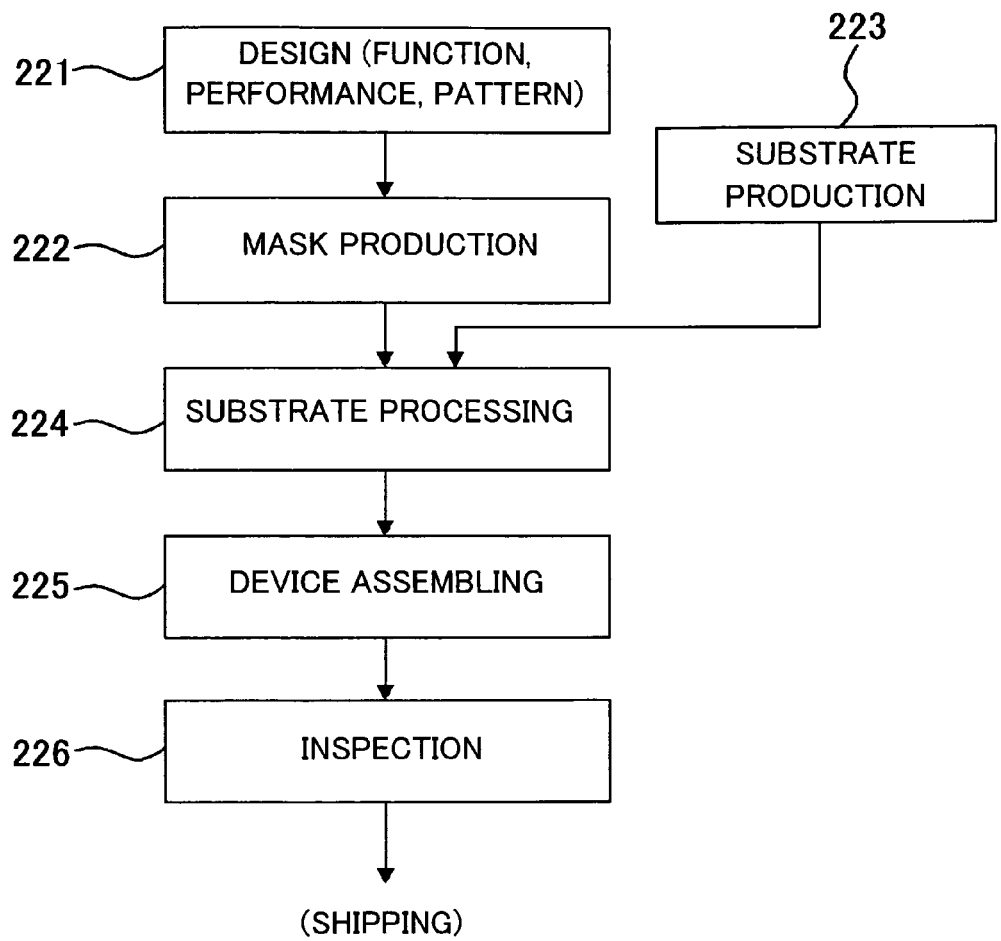
FIG. 8 shows a flow chart illustrating exemplary steps of producing an electronic device.

In a case that an electronic device such as a semiconductor device (or a microdevice) is produced by using the exposure method or the exposure apparatus of the embodiment described above, as shown in FIG. 8, the electronic device is produced by performing, for example, a step 221 of designing the function and the performance of the electronic device; a step 222 of manufacturing a mask (reticle) based on the designing step; a step 223 of producing a substrate (wafer) as a base material for the device and coating the substrate (wafer) with the resist; a substrate-processing step 224 including a step of exposing the substrate (photosensitive substrate) with the pattern of the reticle by the exposure method and the exposure apparatus of the embodiment described above, a step of developing the exposed substrate, a step of heating (curing) and etching the developed substrate, etc.; a step 225 of assembling the device (including processing processes such as a dicing step, a bonding step, a packaging step, etc.); an inspection step 226; and the like.

Therefore, the method for producing the device includes forming the pattern of the photosensitive layer on the substrate by using the exposure method or the exposure apparatus of the embodiment described above, and processing the substrate formed with the pattern (Step 224). According to the exposure apparatus or the exposure method, it is possible to reduce or mitigate the influence of the flare of the projection optical system. Therefore, the electronic device can be produced highly accurately.

The present invention is not limited to the application to the production process for the semiconductor device. The present invention is also widely applicable, for example, to the production process for a display apparatus including, for example, a liquid crystal display element formed on a rectangular glass plate and a plasma display as well as to the production process for various devices including, for example, an image pickup element (CCD, etc.), a micromachine, MEMS (Microelectromechanical Systems), a thin film magnetic head, and a DNA chip, and the mask itself or the like.

The present invention is not limited to the embodiments described above, which may be embodied in other various forms without deviating from the gist or essential characteristics of the present invention.

What is claimed is:

1. A flare-measuring method for measuring flare information of a projection optical system, the flare-measuring method comprising:
arranging at least one aperture pattern of a mask at an object plane of the projection optical system, each aperture pattern of the at least one aperture pattern having a first straight line portion, a second straight line portion that is inclined at a predetermined angle with respect to the first straight line portion, and a first connecting line portion that connects one end of the first straight line portion and one end of the second straight line portion;
irradiating an exposure light onto the at least one aperture pattern and forming an image of the at least one aperture pattern from the mask via the projection optical system onto a photosensitive substrate at an image plane of the projection optical system; and
measuring flare information based on a ratio of (1) a first light amount of the exposure light irradiated onto the at least one aperture pattern to (2) a second light amount of the image of the at least one aperture pattern provided via the projection optical system, wherein
the at least one aperture pattern is defined by the first straight line portion, the second straight line portion and the first connecting line portion, and
the arranging of the at least one aperture pattern comprises arranging a plurality of pairs of the aperture patterns in a scanning direction of the projection optical system, the plurality of pairs of the aperture patterns being oriented in mutually different rotation directions about a point of intersection of a first straight line obtained by extending the first straight line portion and a second straight line obtained by extending the second straight line portion.

2. The flare-measuring method according to claim 1, wherein the forming of the image of the at least one aperture pattern comprises projecting the image of the at least one aperture pattern from the mask onto different positions on the photosensitive substrate, while changing an exposure amount; and
the measuring of the flare information comprises measuring the flare information based on a ratio of (i) a first exposure amount provided when the photosensitive substrate begins to be exposed at a portion that corresponds to the image of the at least one aperture pattern from the mask formed via the projection optical system to (ii) a second exposure amount provided when the photosensitive substrate is exposed at a portion that is in a predetermined positional relationship with respect to the image of the at least one aperture pattern from the mask formed via the projection optical system.

3. The flare-measuring method according to claim 1, wherein
images of the pairs of aperture patterns are successively formed via the projection optical system onto the photosensitive substrate, while moving the exposure light in the predetermined direction relative to the pairs of aperture patterns.

4. The flare-measuring method according to claim 1, wherein the arranging of the at least one aperture pattern further comprises arranging a plurality of lines of the plurality of pairs of the aperture patterns arranged in the scanning direction, in a direction perpendicular to the scanning direction.

5. A mask pattern-correcting method for correcting a mask pattern, the mask pattern-correcting method comprising:
measuring flare information of the projection optical system by the flare-measuring method as defined in claim 1; and
correcting the mask pattern based on a measurement result of the flare information.

6. An exposure method for illuminating a pattern with an exposure light and exposing an object with the exposure light via the pattern and a projection optical system, the exposure method comprising:
measuring flare information of the projection optical system by the flare-measuring method as defined in claim 1;
correcting the pattern as a transfer objective based on a measurement result of the flare information; and
exposing the object with the exposure light via the projection optical system and the corrected pattern as the transfer objective.

7. The flare-measuring method according to claim 1, wherein the arranging of the at least one aperture pattern comprises arranging a first pair of the plurality of pairs of the aperture patterns symmetrically with respect to the point of intersection of the first straight line the second straight line.

8. The flare-measuring method according to claim 7, wherein the plurality of pairs of the aperture patterns have a same shape as that of the first pair of aperture patterns; and
the measuring of the flare information comprises measuring the flare information for each of the rotation directions of each of the plurality of pairs of aperture patterns.

9. The flare-measuring method according to claim 7, wherein the point of intersection is arranged between two aperture patterns constituting the first pair of the aperture patterns.

10. A flare-measuring method for measuring flare information of an optical system, the flare-measuring method comprising:

arranging, at an object plane of the optical system, a predetermined pattern of a mask, the predetermined pattern having:

a first area that extends in a radial direction away from a rotational center, the first area starting at a predetermined position spaced away from the rotational center and spreading at a predetermined opening angle as the first area extends away from the rotational center;

a second area that has a same shape as that of the first area and that is arranged symmetrically to the first area with respect to the rotational center; and a block area that includes the rotational center, located between the first and second areas and having an opposite characteristic regarding transmissivity or reflectivity with respect to a radiation as compared to that of each of the first and second areas;

irradiating the radiation onto the mask to project and form on a photosensitive substrate at an image plane of the optical system an image of the predetermined pattern via the optical system; and measuring flare information either by observing projected images of the first and second areas or by observing a projected image of the block area, wherein the arranging of the predetermined pattern comprises arranging a plurality of the predetermined patterns in a scanning direction of the optical system, extending directions of the plurality of predetermined patterns being oriented in mutually different rotation directions about the rotational center.

11. The flare-measuring method according to claim 10, wherein the arranging of the predetermined pattern further comprises arranging a plurality of lines of the plurality of predetermined patterns arranged in the scanning direction, in a direction perpendicular to the scanning direction.

12. The flare-measuring method according to claim 10, wherein the first area and the second area are arranged along a line which passes through the rotational center.

13. A mask pattern-correcting method for correcting a mask pattern, the mask pattern-correcting method comprising:

measuring flare information of the optical system by the flare-measuring method as defined in claim 10; and correcting the mask pattern based on a measurement result of the flare information.

14. An exposure method for illuminating a patterning mask with the radiation and exposing an object with the radiation via a pattern of the patterning mask and the optical system, the exposure method comprising:

measuring flare information of the optical system by the flare-measuring method as defined in claim 10;

correcting the pattern of the patterning mask based on a measurement result of the flare information; and exposing the object with the radiation via the optical system and the corrected pattern.

15. The exposure method according to claim 14, wherein the radiation is an EUV light, and the first and second areas have reflectivity.

16. The flare-measuring method according to claim 10, wherein:

the predetermined pattern includes a plurality of projection patterns aligned on the mask; and each of the projection patterns includes the first area, the second area, and the block area.

17. The flare-measuring method according to claim 16, further comprising irradiating the radiation onto each of the projection patterns while changing an irradiation amount of the radiation to determine a first irradiation amount EPa provided when an ideal image of the block area is projected onto the photosensitive substrate and to determine a second irradiation amount EPb provided when an image of the block area is eliminated so as to determine a flare amount (%) from the following expression: (EPa/EPb)×100.

* * * * *